United States Patent
Shetty

(10) Patent No.: US 11,141,447 B2
(45) Date of Patent: Oct. 12, 2021

(54) COMPOSITION FOR TREATMENT AND MANAGEMENT OF ADDICTION AND METHOD OF PREPARATION THEREOF

(71) Applicant: Muniyal Ayurvedic Research Centre, Manipal (IN)

(72) Inventor: M Vijayabhanu Shetty, Karnataka (IN)

(73) Assignee: Muniyal Ayurvedic Research Centre, Manipal (IN)

( * ) Notice: Subject to any disclaimer, the term of this patent is extended or adjusted under 35 U.S.C. 154(b) by 101 days.

(21) Appl. No.: 16/585,645

(22) Filed: Sep. 27, 2019

(65) Prior Publication Data

US 2020/0023027 A1    Jan. 23, 2020

Related U.S. Application Data

(60) Provisional application No. 62/748,954, filed on Oct. 22, 2018.

(51) Int. Cl.

| | | |
|---|---|---|
| *A61K 36/47* | (2006.01) |
| *A61P 25/34* | (2006.01) |
| *A61K 36/75* | (2006.01) |
| *A61K 36/53* | (2006.01) |
| *A61K 36/81* | (2006.01) |
| *A61K 36/48* | (2006.01) |
| *A61K 36/886* | (2006.01) |
| *A61K 36/58* | (2006.01) |
| *A61K 36/59* | (2006.01) |
| *A61K 36/68* | (2006.01) |
| *A61K 36/882* | (2006.01) |
| *A61K 36/37* | (2006.01) |
| *A61K 36/35* | (2006.01) |
| *A61K 36/24* | (2006.01) |
| *A61K 9/20* | (2006.01) |
| *A61P 25/32* | (2006.01) |
| *A61K 36/28* | (2006.01) |

(52) U.S. Cl.
CPC .............. *A61K 36/47* (2013.01); *A61K 9/205* (2013.01); *A61K 36/24* (2013.01); *A61K 36/28* (2013.01); *A61K 36/35* (2013.01); *A61K 36/37* (2013.01); *A61K 36/48* (2013.01); *A61K 36/53* (2013.01); *A61K 36/58* (2013.01); *A61K 36/59* (2013.01); *A61K 36/68* (2013.01); *A61K 36/75* (2013.01); *A61K 36/81* (2013.01); *A61K 36/882* (2013.01); *A61K 36/886* (2013.01); *A61P 25/32* (2018.01); *A61P 25/34* (2018.01)

(58) Field of Classification Search
None
See application file for complete search history.

(56) References Cited

U.S. PATENT DOCUMENTS 5,405,613 A * 4/1995 Rowland ................ A61K 35/04
424/439

* cited by examiner

*Primary Examiner* — Terry A McKelvey
*Assistant Examiner* — Catheryne Chen
(74) *Attorney, Agent, or Firm* — Pilloff Passino & Cosenza LLP; Sean A. Passino; Rachel K. Pilloff

(57) ABSTRACT

Composition for treatment and management of addiction and method of preparation thereof are disclosed herein. The disclosed herbal composition includes herb and mineral which facilitate in treating addiction. It may be used to treat addiction such as alcohol addiction, tobacco addiction, excessive smoking, drugs abuse etc. Further, the disclosed composition may also be instrumental in treating complications associated with addiction and withdrawal symptoms.

25 Claims, 7 Drawing Sheets

Vehicle control

Alcohol + Vehicle

Alcohol + Silymarin (100 mg/kg)

Alcohol + TEST DRUG (30 mg/kg, p.o)

Alcohol + TEST DRUG (100 mg/kg, p.o)

TEST DRUG (100 mg/kg, p.o)

COMPOSITION FOR TREATMENT AND MANAGEMENT OF ADDICTION AND METHOD OF PREPARATION THEREOF

CROSS REFERENCE TO RELATED APPLICATION

This application is based on and derives the benefit of U.S. Provisional Application 62/748,954 filed on the 22 Oct. 2018, the contents of which are incorporated herein by reference in their entirety.

TECHNICAL FIELD

The embodiments disclosed in this specification relate to herbal compositions, and more particularly to composition and method useful in treatment of individuals having addiction to substances such as alcohol, tobacco and drugs. It also relates to the process of preparation of such composition.

BACKGROUND

Addiction is a major problem affecting many throughout the world. It is not just a personal problem but also a social illness as it leads to violence, drunken driving, child abuse, stress, increase in crime rate, unhappy families and so on. Substance abuse, such as overuse of alcohol, tobacco and drugs, leads to health problems that affect, both, mind and body. While the excessive use of these addictive substances has evident toxic effects on vital organ such as liver, kidney, lungs, etc, it also causes psychological harm, leading to domestic unrest, anxiety, depression, suicidal and homicidal behaviors, etc.

Alcoholism has detrimental effects on human body. It leads to complications such as liver inflammation, liver cirrhosis, fatty liver, cardiomyopathy, Arrhythmias, Stroke, etc. It has also been found to increase the risk of cancer of mouth, throat, esophagus, etc. Alcohol has been found to be a leading risk factor for chronic diseases and injuries. Alcohol has been identified to account for around 3.8% of deaths and 4.6% of disability-adjusted life-years (DALY), globally (Rehm J, Mathers C, Popova S, Thavorncharoensap M, Teerawattananon Y, Patra J (2009). *Lancet*. June 27; 373(9682):2223-33.doi: 10.1016/S0140-6736(09)60746-7).

Nicotine is another habit-forming substance. Tobacco use is extremely harmful and could lead to cardiovascular diseases, pulmonary diseases, cancer, sexual dysfunction etc. Smoking is considered to reduce the life expectancy by around 10 to 12 years. Tobacco is considered a leading preventable cause of death killing more people than AIDS, tuberculosis and malaria combined, globally. (Gauravi A. Mishra, Sharmila A. Pimple, and Surendra S. Shastri. *Indian J Med Paediatr Oncol.* 2012 July-September; 33(3): 139-145.doi: 10.4103/0971-5851.103139)

Various methods are known to treat addiction, such as counselling, Antabuse drugs, nicotine replacement therapies, etc. Further, various methods of detoxification and re-habilitation are also well known to help overcome addiction. The currently available Antabuse drugs cause unpleasant side effects such as vomiting, headaches, nausea, etc. Antabuse drugs may also cause severe side effects such as heart attacks, breathing problems, coma, etc. Symptomatic treatment methods may be also used which include treatment of depression and anxiety caused by addiction. Such treatment option may in turn lead to dependency and pronounced withdrawal symptoms.

Alternatively, ayurvedic interventions are also known to treat addiction. Many methods of de-addiction and de-toxification have previously been developed. The use of herbs such as *Pueraria lobate, Panax notoginseng*, etc in compositions to treat alcohol dependence and de-toxification is well known. However, there exists a need for an effective method of better treatment/management of addiction.

OBJECTS OF THE DISCLOSED EMBODIMENTS

The principal object of the embodiments disclosed herein is to provide an herbal composition for treatment of addiction and associated complications.

A second object of the embodiments disclosed herein is to provide a method for the treatment of addiction and associated complications.

Another object of the embodiments disclosed herein is to provide a composition for alleviating clinical symptoms associated with addiction of alcohol, tobacco, drugs etc.

An object of the embodiments disclosed herein is to provide a composition for alleviating withdrawal symptoms associated with addiction of alcohol, tobacco, drugs etc.

Another object of the embodiments disclosed herein is to provide a composition having hepatoprotective and restorative effect in patients with addiction induced liver disorders.

A further object of the embodiments disclosed herein is to provide a composition and method of preventing addiction recurrence.

Yet another object of the embodiments disclosed herein is to provide a herbal composition and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are further illustrated in the accompanying drawings. The embodiments herein will be better understood from the following description with reference to the drawings, in which.

DETAILED DESCRIPTION

Figure 1:
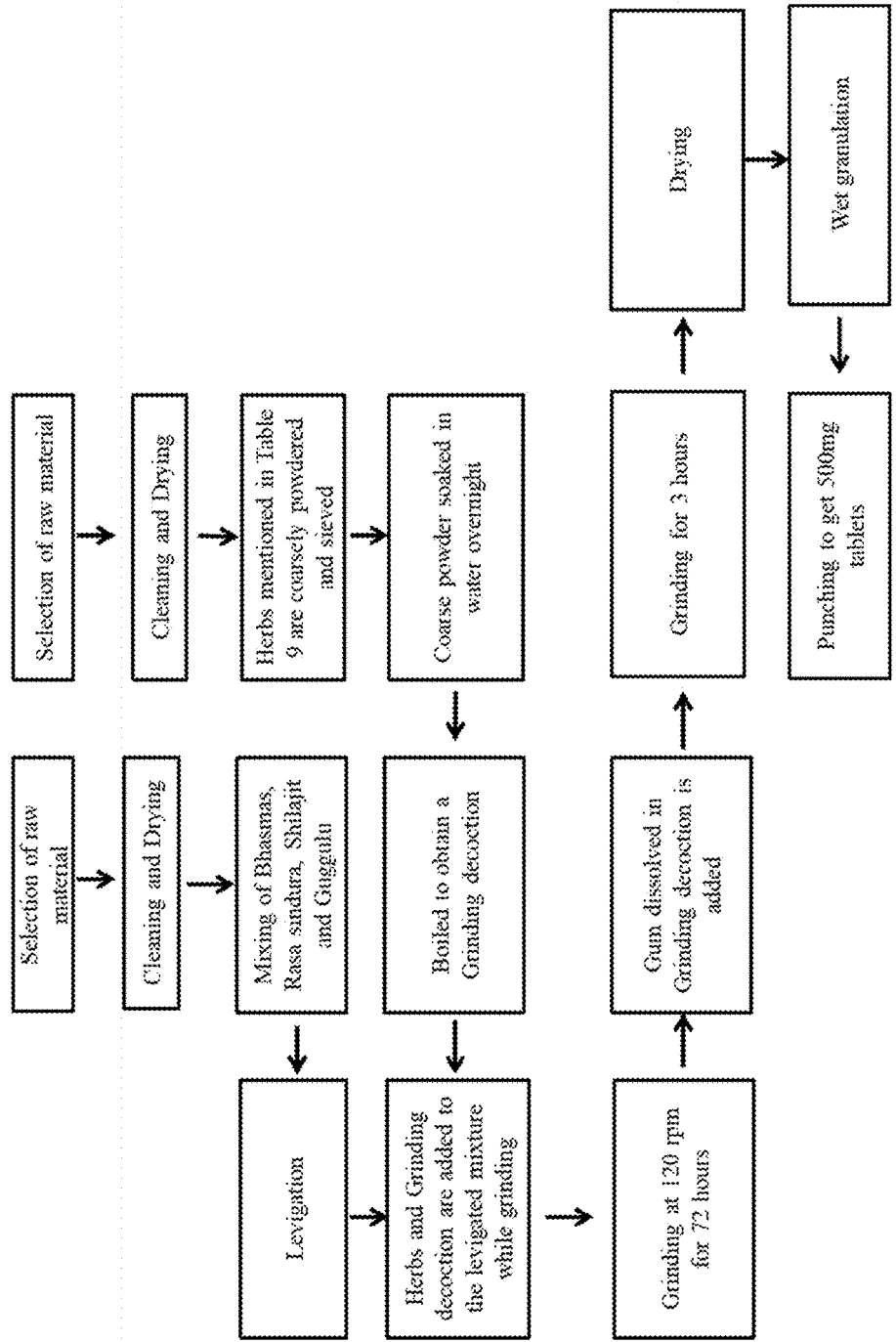
FIG. 1 is a flowchart depicting the preparation of the disclosed composition in the form of fortified tablets.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve an herbal composition of therapeutic value, and a process for preparation of the herbal composition. The herbal composition disclosed herein is useful in the treatment of addiction. Addiction according to the various embodiments herein include use/abuse of addictive substances which include, but not limited to, habit-forming substances, alcohol, cigarette smoking, tobacco chewing, drugs etc. It has also been observed that the embodiments of the disclosed composition are instrumental in treatment and management of withdrawal symptoms associated with addiction such as tremors, headache, restlessness, anxiety, depression, constipation, insomnia, coughing etc. Further, it has also been observed that the embodiments of the disclosed composition are effective in treatment and management of complications associated with addiction such as fatty liver, liver cirrhosis, renal disorder etc. Accordingly, embodiments disclosed herein achieve a method for treatment and management of addiction and associated complications. Further disclosed are embodiments for alleviating clinical symptoms associated with addiction, such as asthenia, easy fatigability, tiredness, nausea, anorexia, abdominal discomfort, abdominal pain, stool frequency, and muscle cramps. The disclosed embodiments herein also provide a composition having hepatoprotective and liver restorative properties in patients suffering from addiction induced liver disorders. The various embodiments disclosed herein further provide a composition and method of preventing addiction recurrence.

Composition

The disclosed embodiments herein provide herbal composition having a combination of selected herbs and minerals. In an embodiment, the herbal composition includes at least one herb and at least one mineral. In another embodiment, the herbal composition includes at least one herb, at least one mineral and at least one suitable excipient.

Herb

In an embodiment, the composition includes the herbs *Phyllanthus niruri, Eclipta alba, Boerhavia diffusa, Swertia chirata, Embelia ribes, Acacia catechu, Plumbago zeylanica, Terminalia arjuna, Pueraria tuberosa, Commiphora mukul* and *Picrorhiza kurroa* or their extracts, or the active ingredients extracted from these herbs. In another embodiment, the composition further includes at least one herb selected from *Emblica officinalis, Terminalia chebula, Terminalia bellerica, Piper longum, Piper nigrum, Zingiber officinalis, Aegle marmelos, Premna mucronata, Oroxylum indicum, Stereospermum suaveolens, Gmelina arborea, Solanum indicum, Solanum xanthocarpum, Tribulus terrestris, Uraria picta, Desmodium gangeticum, Bacopa monnieri, Convolvulus pluricaulis, Mucuna pruriens, Nardostachys jatamansi, Rauwolfia serpentina, Withania somnifera, Acorus calamus, Santalum album, Pterocarpus santalinus, Glycyrrhiza glabra, Inula racemosa, Sida cordifolia, Cinnamomum zeylanica, Elettaria cardamomum, Ocimum sanctum, Tinospora cordifolia, Vetiveria zizanioides, Hemidesmus indicus, Pluchea lanceolata, Cassia fistula, Prunus cerasoides, Rubia cordifolia, Ricinus communis* and *Mesua ferrea*, or their extracts, or the active ingredients extracted from these herbs.

The composition may include a specific part of the herb (also referred as herb component) such as roots, flowers, fruits, stem, bark, resin, rhizome, whole plant, extract etc. In an embodiment, the composition may include whole plant of *Phyllanthus niruri*, whole plant of *Eclipta alba*, roots of *Boerhavia diffusa*, whole plant of *Swertia chirata*, fruit of *Embelia ribes*, heartwood of *Acacia catechu*, root of *Plumbago zeylanica*, stem bark of *Terminalia arjuna*, tuber of *Pueraria tuberosa*, gum resin of *Commiphora Mukul* and root of *Picrorhiza kurroa*; or their extract. In another embodiment the composition includes fruit of *Emblica officinalis, Terminalia chebula, Terminalia bellerica, Piper longum, Tribulus terrestris* and *Piper nigrum*; rhizome of *Zingiber officinalis, Acorus calamus* and *Nardostachys jatamansi*; root of *Aegle marmelos, Premna mucronata, Glycyrrhiza glabra, Inula racemosa, Sida cordifolia, Rauwolfia serpentina, Rubia cordifolia, Vetiveria zizanioides, Hemidesmus indicus, Pluchea lanceolata, Elettaria cardamomum, Withania somnifera, Oroxylum indicum, Stereospermum suaveolens, Urania picta, Desmodium gangeticum, Gmelina arborea, Solanum indicum* and *Solanum xanthocarpum*; whole plant of *Bacopa monnieri* and *Convolvulus pluricaulis*; seeds of *Mucuna pruriens*; heartwood of *Santalum album, Prunus cerasoides* and *Pterocarpus santalinus*; stem bark of *Cinnamomum zeylanica* and *Cassia fistula*, leaves of *Ocimum sanctum* and *Ricinus communis*, stem of *Tinospora cordifolia* and stamen of *Mesua ferrea*. However, it is also within the scope of the claims provided herein for the herbal composition to include other herb components such as leaf, flowers, etc. without otherwise deterring intended function of the herbal composition.

The herb component maybe included in the composition in any form that is generally known in the field. For example, the herb component may be dried, powdered, processed to form concentrates, extracted etc. In one preferred embodiment, the herb components are in dry powder form which is incorporated into the composition. In an embodiment, the herb components are in the form of fine powder sieved at 80 mesh screen which is incorporated into the composition. In another embodiment, the herb components may be included in the composition in the form of extracts. The extracts of herbs may be prepared using solvents such as lower alcohols, water, and mixtures thereof.

In an embodiment, the herb components may be included in the composition in the form of aqueous extract or alcohol extract or both. The aqueous and alcohol extracts of herbs that may be used may be prepared by techniques that are known in the field.

In an embodiment, the composition comprises *Phyllanthus niruri* in an amount in the range of 4 to 8 wt. %; *Eclipta alba niruri* in an amount in the range of 2 to 6 wt. %; *Boerhavia diffusa* in an amount in the range of 2 to 6 wt. %; *Swertia chirata* in an amount in the range of 2 to 6 wt. %; *Embelia ribes* in an amount in the range of 2 to 6 wt. %; *Acacia catechu* in an amount in the range of 2 to 6 wt. %; *Pueraria tuberosa* in an amount in the range of 2 to 6 wt. %; *Plumbago zeylanica* in an amount in the range of 6 to 10 wt. %; *Terminalia arjuna* in an amount in the range of 6 to 10 wt. %; *Commiphora mukul* in an amount of ≤3 wt. %; and *Picrorhiza kurroa* in an amount in the range of 6 to 10 wt. %, of the total weight of the composition.

In another embodiment, the composition further includes at least one ingredient selected from the group consisting of *Emblica officinalis, Terminalia chebula, Terminalia bellerica, Piper longum, Piper nigrum, Zingiber officinalis, Aegle marmelos, Premna mucronata, Oroxylum indicum, Stereospermum suaveolens, Gmelina arborea, Solanum indicum, Solanum xanthocarpum, Tribulus terrestris, Uraria picta, Desmodium gangeticum, Bacopa monnieni, Convolvulus pluricaulis, Mucuna pruriens, Nardostachys jatamansi, Rauwolfia serpentina, Withania somnifera, Acorus calamus, Santalum album, Pterocarpus santalinus, Glycyrrhiza glabra, Inula racemosa, Sida cordifolia, Cinnamomum zeylanica, Elettaria cardamomum, Ocimum sanctum, Tinospora cordifolia, Vetiveria zizanioides, Hemidesmus indicus, Pluchea lanceolata, Cassia fistula, Prunus cerasoides, Rubia cordifolia, Ricinus communis* and *Mesua ferrea*, wherein each of the ingredients is present in an amount of ≤3 wt. % of the total weight of the composition.

In an embodiment, the composition further includes at least one ingredient selected from the group consisting of *Emblica officinalis* in an amount of ≤2 wt. %, *Terminalia chebula* in an amount of ≤2 wt. %, *Terminalia bellerica* in an amount of ≤2 wt. %, *Piper longum* in an amount of ≤2 wt. %, *Piper nigrum* in an amount of ≤2 wt. %, *Zingiber officinalis* in an amount of ≤2 wt. %, *Aegle marmelos* in an amount of ≤2 wt. %, *Premna mucronata* in an amount of ≤2 wt. %, *Oroxylum indicum* in an amount of ≤2 wt. %, *Stereospermum suaveolens* in an amount of ≤2 wt. %, *Gmelina arborea* in an amount of ≤2 wt. %, *Solanum indicum* in an amount of ≤2 wt. %, *Solanum xanthocarpum* in an amount of ≤2 wt. %, *Tribulus terrestris* in an amount of ≤2 wt. %, *Uraria picta* in an amount of ≤2 wt. %, *Desmodium gangeticum* in an amount of ≤2 wt. %, *Bacopa monnieri* in an amount of ≤3 wt. %, *Convolvulus pluricaulis* in an amount of ≤2 wt. %, *Mucuna pruriens* in an amount of ≤2 wt. %, *Nardostachys jatamansi* in an amount of ≤3 wt. %, *Rauwolfia serpentina* in an amount of ≤2 wt. %, *Withania somnifera* in an amount of ≤3 wt. %, *Acorus calamus* in an amount of ≤2 wt. %, *Santalum album* in an amount of ≤2 wt. %, *Pterocarpus santalinus* in an amount of ≤2 wt. %, *Glycyrrhiza glabra* in an amount of ≤2 wt. %, *Inula racemosa* in an amount of ≤3 wt. %, *Sida cordifolia* in an amount of ≤2 wt. %, *Cinnamomum zeylanica* in an amount of ≤2 wt. %, *Elettaria cardamomum* in an amount of ≤2 wt. %, *Ocimum sanctum* in an amount of ≤2 wt. %, *Tinospora cordifolia* in an amount of ≤2 wt. %, *Vetiveria zizanioides* in an amount of ≤2 wt. %, *Hemidesmus indicus* in an amount of ≤2 wt. %, *Pluchea lanceolata* in an amount of ≤2 wt. %, *Cassia fistula* in an amount of ≤2 wt. %, *Prunus cerasoides* in an amount of ≤2 wt. %, *Rubia cordifolia* in an amount of ≤2 wt. %, *Ricinus communis* in an amount of ≤2 wt. % and *Mesua ferrea* in an amount of ≤2 wt. %, of the total weight of the composition.

Mineral

In an embodiment, the composition includes at least one bhasma selected from the group consisting of Mukta shukti bhasma, Swarna makshika bhasma, Rajata bhasma, Pravala bhasma, Shringa bhasma, Yashada bhasma, Vanga bhasma, Shankha bhasma, Loha bhasma, Abhraka bhasma, Tamra bhasma and Mandura bhasma. Alternatively, the mineral may also be selected from the following mineral in incinerated form: calcium carbonate, copper pyrite, silver, zinc, iron, mica, hart's horn, copper and iron rust.

The disclosed composition may include each of the bhasmas in an amount of ≤2 wt. %. In an embodiment, the composition includes at least one bhasma selected from the group consisting of Mukta shukti bhasma in an amount of ≤1 wt. %, Swarna makshika bhasma in an amount of ≤1 wt. %, Rajata bhasma in an amount of ≤1 wt. %, Pravala bhasma in an amount of ≤1 wt. %, Shringa bhasma in an amount of ≤1 wt. %, Yashada bhasma in an amount of ≤1 wt. %, Vanga bhasma in an amount of ≤1 wt. %, Shankha bhasma in an amount of ≤1 wt. %, Loha bhasma in an amount of ≤2 wt. %, Abhraka bhasma in an amount of ≤2 wt. %, Tamra bhasma in an amount of ≤1 wt. %, and Mandura bhasma in an amount of ≤1 wt. %, of the total composition.

In an embodiment, the composition includes Rasasindura. In the various embodiments herein, Rasasindura is a mercurial preparation which is a sublime product of a mixture of mercury and sulfur. In an embodiment, the composition includes Rasasindura in an amount of ≤1 wt. % of the total composition.

In another embodiment, the composition comprises Shilajit. Shilajit (also known as *Asphaltum punjabianum*) is a blackish brown mineral resin. In an embodiment, the composition includes Shilajit in an amount of ≤3 wt. % of the total composition. However, it is also within the scope of claims provided herewith for the herbal composition to include, as a substitute or additionally, other similar calcined preparations, mercurial preparations, resins and/or minerals without otherwise deterring from the intended function of the herbal composition.

The disclosed composition, in the various embodiments herein, may further include a suitable excipient. The suitable excipients include solvents, binders, lubricants, herbal carriers, oils and salts that are generally known in the art. In an embodiment, the suitable excipient comprises of Gum acacia. In an embodiment, the composition includes Gum acacia in an amount in the range of 8 to 10 wt. % of the total composition. In an embodiment, every 500 mg of the composition comprises 50 mg of gum acacia.

In an embodiment, the composition includes *Phyllanthus niruri* (4 to 8 wt. %), *Eclipta alba* (2 to 6 wt. %), *Boerhavia diffusa* (2 to 6 wt. %), *Swertia chirata* (2 to 6 wt. %), *Embelia ribes* (2 to 6 wt. %), *Acacia catechu* (2 to 6 wt. %), *Pueraria tuberosa* (2 to 6 wt. %), *Plumbago zeylanica* (6 to 10 wt. %), *Terminalia arjuna* (6 to 10 wt. %), *Commiphora mukul* (≤1 wt. %), *Picrorhiza kurroa* (6 to 10 wt. %); at least one bhasma selected from the group consisting of Mukta shukti bhasma (≤1 wt. %), Swarna makshika bhasma (≤1 wt. %), Rajata bhasma (≤1 wt. %), Pravala bhasma (≤1 wt. %), Shringa bhasma (≤1 wt. %), Yashada bhasma (≤1 wt. %), Vanga bhasma (≤1 wt. %), Shankha bhasma (≤1 wt. %), Loha bhasma (≤2 wt. %), Abhraka bhasma (≤2 wt. %), Tamra bhasma (≤1 wt. %) and Mandura bhasma (≤1 wt. %); Shilajit (≤3 wt. %); and Rasasindura (≤1 wt. %), of the total weight of the composition.

In another embodiment, the composition includes *Phyllanthus niruri* (4 to 8 wt. %), *Eclipta alba* (2 to 6 wt. %), *Boerhavia diffusa* (2 to 6 wt. %), *Swertia chirata* (2 to 6 wt. %), *Embelia ribes* (2 to 6 wt. %), *Acacia catechu* (2 to 6 wt. %), *Pueraria tuberosa* (2 to 6 wt. %), *Plumbago zeylanica* (6 to 10 wt. %), *Terminalia arjuna* (6 to 10 wt. %), *Commiphora mukul* (≤1 wt. %), *Picrorhiza kurroa* (6 to 10 wt. %); at least one bhasma selected from the group consisting of Mukta shukti bhasma (≤1 wt. %), Swarna makshika bhasma (≤1 wt. %), Rajata bhasma (≤1 wt. %), Pravala bhasma (≤1 wt. %), Shringa bhasma (≤1 wt. %), Yashada bhasma (≤1 wt. %), Vanga bhasma (≤1 wt. %), Shankha bhasma (≤1 wt. %), Loha bhasma (≤2 wt. %), Abhraka bhasma (≤2 wt. %), Tamra bhasma (≤1 wt. %) and Mandura bhasma (≤1 wt. %); Shilajit (≤3 wt. %); Rasasindura (≤1 wt. %); and Gum acacia (8 to 12 wt %), of the total weight of the composition.

In an embodiment, the composition includes *Phyllanthus niruri* (6 wt. %), *Eclipta alba* (4 wt. %), *Boerhavia diffusa* (4 wt. %), *Swertia chirata* (4 wt. %), *Embelia ribes* (4 wt. %), *Acacia catechu* (4 wt. %), *Pueraria tuberosa* (4 wt. %), *Plumbago zeylanica* (8 wt. %), *Terminalia arjuna* (8 wt. %), *Commiphora mukul* (≤1 wt. %), *Picrorhiza kurroa* (8 wt. %); at least one bhasma selected from the group consisting of Mukta shukti bhasma (≤1 wt. %), Swarna makshika bhasma (≤1 wt. %), Rajata bhasma (≤1 wt. %), Pravala bhasma (≤1 wt. %), Shringa bhasma (≤1 wt. %), Yashada bhasma (≤1 wt. %), Vanga bhasma (≤1 wt. %), Shankha bhasma (≤1 wt. %), Loha bhasma (≤2 wt. %), Abhraka bhasma (≤2 wt. %), Tamra bhasma (≤1 wt. %) and Mandura bhasma (≤1 wt. %); Shilajit (≤3 wt. %); Rasasindura (≤1 wt. %); and Gum acacia (10 wt %), of the total weight of the composition.

In another embodiment, the composition includes *Phyllanthus niruri* (4 to 8 wt. %), *Eclipta alba* (2 to 6 wt. %), *Boerhavia diffusa* (2 to 6 wt. %), *Swertia chirata* (2 to 6 wt. %), *Embelia ribes* (2 to 6 wt. %), *Acacia catechu* (2 to 6 wt. %) and *Pueraria tuberosa* (2 to 6 wt. %), *Plumbago zeylanica* (6 to 10 wt. %), *Terminalia arjuna* (6 to 10 wt. %), *Picrorhiza kurroa* (6 to 10 wt. %), *Commiphora mukul* (≤1 wt. %), *Emblica officinalis* (≤2 wt. %), *Terminalia chebula* (≤2 wt. %), *Terminalia bellerica* (≤2 wt. %), *Piper longum* (≤2 wt. %), *Piper nigrum* (≤2 wt. %), *Zingiber officinalis* (≤2 wt. %), *Aegle marmelos* (≤2 wt. %), *Premna mucronata* (≤2 wt. %), *Oroxylum indicum* (≤2 wt. %), *Stereospermum suaveolens* (≤2 wt. %), *Gmelina arborea* (≤2 wt. %), *Solanum indicum* (≤2 wt. %), *Solanum xanthocarpum* (≤2 wt. %), *Tribulus terrestris* (≤2 wt. %), *Uraria picta* (≤2 wt. %), *Desmodium gangeticum* (≤2 wt. %), *Bacopa monnieri* (≤3 wt. %), *Convolvulus pluricaulis* (≤2 wt. %), *Mucuna pruriens* (≤2 wt. %), *Nardostachys jatamansi* (≤3 wt. %), *Rauwolfia serpentina* (≤2 wt. %), *Withania somnifera* (≤3 wt. %), *Acorus calamus* (≤2 wt. %), *Santalum album* (≤2 wt. %), *Pterocarpus santalinus* (≤2 wt. %), *Glycyrrhiza glabra* (≤2 wt. %), *Inula racemosa* (≤3 wt. %), *Sida cordifolia* (≤2 wt. %), *Cinnamomum zeylanica* (≤2 wt. %), *Elettaria cardamomum* (≤2 wt. %), *Ocimum sanctum* (≤2 wt. %), *Tinospora cordifolia* (≤2 wt. %), *Vetiveria zizanioides* (≤2 wt. %), *Hemidesmus indicus* (≤2 wt. %), *Pluchea lanceolata* (≤2 wt. %), *Cassia fistula* (≤2 wt. %), *Prunus cerasoides* (≤2 wt. %), *Rubia cordifolia* (≤2 wt. %), *Ricinus communis* (≤2 wt. %) and *Mesua ferrea* (≤2 wt. %), Mukta shukti bhasma (≤1 wt. %), Swarna makshika bhasma (≤1 wt. %), Rajata bhasma 1 wt. %), Pravala bhasma (≤1 wt. %), Shringa bhasma (≤1 wt. %), Yashada bhasma 1 wt. %), Vanga bhasma 1 wt. %), Shankha bhasma 1 wt. %), Loha bhasma (≤2 wt. %), Abhraka bhasma (≤2 wt. %), Tamra bhasma 1 wt. %), Mandura bhasma 1 wt. %), Rasasindura (≤1 wt. %) and Shilajit (≤3 wt. %), of the total weight of the composition.

In an embodiment, the composition includes *Phyllanthus niruri* (4 to 8 wt. %), *Eclipta alba* (2 to 6 wt. %), *Boerhavia diffusa* (2 to 6 wt. %), *Swertia chirata* (2 to 6 wt. %), *Embelia ribes* (2 to 6 wt. %), *Acacia catechu* (2 to 6 wt. %) and *Pueraria tuberosa* (2 to 6 wt. %), *Plumbago zeylanica* (6 to 10 wt. %), *Terminalia arjuna* (6 to 10 wt. %), *Picrorhiza kurroa* (6 to 10 wt. %), *Commiphora mukul* (≤1 wt. %), *Emblica officinalis* (≤2 wt. %), *Terminalia chebula* (≤2 wt. %), *Terminalia bellerica* (≤2 wt. %), *Piper longum* (≤2 wt. %), *Piper nigrum* (≤2 wt. %), *Zingiber officinalis* (≤2 wt. %), *Aegle marmelos* (≤2 wt. %), *Premna mucronata* (≤2 wt. %), *Oroxylum indicum* (≤2 wt. %), *Stereospermum suaveolens* (≤2 wt. %), *Gmelina arborea* (≤2 wt. %), *Solanum indicum* (≤2 wt. %), *Solanum xanthocarpum* (≤2 wt. %), *Tribulus terrestris* (≤2 wt. %), *Uraria picta* (≤2 wt. %), *Desmodium gangeticum* (≤2 wt. %), *Bacopa monnieri* (≤3 wt. %), *Convolvulus pluricaulis* (≤2 wt. %), *Mucuna pruriens* (≤2 wt. %), *Nardostachys jatamansi* (≤3 wt. %), *Rauwolfia serpentina* (≤2 wt. %), *Withania somnifera* (≤3 wt. %), *Acorus calamus* (≤2 wt. %), *Santalum album* (≤2 wt. %), *Pterocarpus santalinus* (≤2 wt. %), *Glycyrrhiza glabra* (≤2 wt. %), *Inula racemosa* (≤3 wt. %), *Sida cordifolia* (≤2 wt. %), *Cinnamomum zeylanica* (≤2 wt. %), *Elettaria cardamomum* (≤2 wt. %), *Ocimum sanctum* (≤2 wt. %), *Tinospora cordifolia* (≤2 wt. %), *Vetiveria zizanioides* (≤2 wt. %), *Hemidesmus indicus* (≤2 wt. %), *Pluchea lanceolata* (≤2 wt. %), *Cassia fistula* (≤2 wt. %), *Prunus cerasoides* (≤2 wt. %), *Rubia cordifolia* (≤2 wt. %), *Ricinus communis* (≤2 wt. %) and *Mesua ferrea* (≤2 wt. %), Mukta shukti bhasma (≤1 wt. %), Swarna makshika bhasma (≤1 wt. %), Rajata bhasma 1 wt. %), Pravala bhasma (≤1 wt. %), Shringa bhasma (≤1 wt. %), Yashada bhasma 1 wt. %), Vanga bhasma 1 wt. %), Shankha bhasma 1 wt. %), Loha bhasma (≤2 wt. %), Abhraka bhasma (≤2 wt. %), Tamra bhasma 1 wt. %), Mandura bhasma 1 wt. %), Rasasindura 1 wt. %), Shilajit (≤3 wt. %) and Gum acacia (8 to 12 wt. %), of the total weight of the composition.

In an embodiment, the composition includes *Phyllanthus niruri* (6 wt. %), *Eclipta alba* (4 wt. %), *Boerhavia diffusa* (4 wt. %), *Swertia chirata* (4 wt. %), *Embelia ribes* (4 wt. %), *Acacia catechu* (4 wt. %) and *Pueraria tuberosa* (4 wt. %), *Plumbago zeylanica* (8 wt. %), *Terminalia arjuna* (8 wt. %), *Picrorhiza kurroa* (8 wt. %), *Commiphora mukul* (≤1 wt. %), *Emblica officinalis* (≤2 wt. %), *Terminalia chebula* (≤2 wt. %), *Terminalia bellerica* (≤2 wt. %), *Piper longum* (≤2 wt. %), *Piper nigrum* (≤2 wt. %), *Zingiber officinalis* (≤2 wt. %), *Aegle marmelos* (≤2 wt. %), *Premna mucronata* (≤2 wt. %), *Oroxylum indicum* (≤2 wt. %), *Stereospermum suaveolens* (≤2 wt. %), *Gmelina arborea* (≤2 wt. %), *Solanum indicum* (≤2 wt. %), *Solanum xanthocarpum* (≤2 wt. %), *Tribulus terrestris* (≤2 wt. %), *Uraria picta* (≤2 wt. %), *Desmodium gangeticum* (≤2 wt. %), *Bacopa monnieri* (≤3 wt. %), *Convolvulus pluricaulis* (≤2 wt. %), *Mucuna pruriens* (≤2 wt. %), *Nardostachys jatamansi* (≤3 wt. %), *Rauwolfia serpentina* (≤2 wt. %), *Withania somnifera* (≤3 wt. %), *Acorus calamus* (≤2 wt. %), *Santalum album* (≤2 wt. %), *Pterocarpus santalinus* (≤2 wt. %), *Glycyrrhiza glabra* (≤2 wt. %), *Inula racemosa* (≤3 wt. %), *Sida cordifolia* (≤2 wt. %), *Cinnamomum zeylanica* (≤2 wt. %), *Elettaria cardamomum* (≤2 wt. %), *Ocimum sanctum* (≤2 wt. %), *Tinospora cordifolia* (≤2 wt. %), *Vetiveria zizanioides* (≤2 wt. %), *Hemidesmus indicus* (≤2 wt. %), *Pluchea lanceolata* (≤2 wt. %), *Cassia fistula* (≤2 wt. %), *Prunus cerasoides* (≤2 wt.

%), *Rubia cordifolia* (≤2 wt. %), *Ricinus communis* (≤2 wt. %) and *Mesua ferrea* (≤2 wt. %), Mukta shukti bhasma (≤1 wt. %), Rajata bhasma (≤1 wt. %), Swarna makshika bhasma (≤1 wt. %), Pravala bhasma 1 wt. %), Shringa bhasma (≤1 wt. %), Yashada bhasma (≤1 wt. %), Vanga bhasma 1 wt. %), Shankha bhasma 1 wt. %), Loha bhasma (≤2 wt. %), Abhraka bhasma (≤2 wt. %), Tamra bhasma (≤1 wt. %), Mandura bhasma 1 wt. %), Rasasindura (≤1 wt. %), Shilajit (≤3 wt. %) and Gum acacia (10 wt. %), of the total weight of the composition. However, it is apparent that slight variations in the amount of the ingredients may be performed without otherwise deterring from the intended function of the herbal composition.

The herbal composition disclosed herein may be formulated in various dosage forms such that it is suitable for oral administration. The herbal composition may be in the form of tablets, pellets, lozenges, granules, capsules, solutions, emulsions, suspensions, or any other form suitable for use. In an embodiment, the herbal composition is formulated in the form of tablets, such as 500 mg tablets. For example: Table 1 depicts the quantities of each ingredient in a 500 mg tablet. All weight percentages are based on the total weight of the composition.

Disclosed herein, is a tablet for treating addiction and associated complications. In an embodiment, the tablet is a 500 mg tablet having herb, mineral and an excipient as depicted in Table 1.

TABLE 1

Each 500 mg tablet includes:

| NO. | SANSKRIT NAME | PART USED | SCIENTIFIC NAME | QUANTITY |
|---|---|---|---|---|
| Key ingredients: | | | | |
| 1. | Bhumyamalaki | Dry whole plant | *Phyllanthus niruri* | 30 mg |
| 2. | Bhringaraja | Dry whole plant | *Eclipta alba* | 20 mg |
| 3. | Punarnava | Dry root | *Boerhavia diffusa* | 20 mg |
| 4. | Kiratha | Dry whole plant | *Swertia chirata* | 20 mg |
| 5. | Vidanga | Dry fruit | *Embelia ribes* | 20 mg |
| 6. | Khadira | Dry heartwood | *Acacia catechu* | 20 mg |
| 7. | Shuddha Chitraka | Dry purified root | *Plumbago zeylanica* | 40 mg |
| 8. | Arjuna | Dry stem bark | *Terminalia arjuna* | 40 mg |
| 9. | Vidarikanda | Dry tuber | *Pueraria tuberosa* | 20 mg |
| 10. | Katuki | Dry root | *Picrorhiza kurroa* | 40 mg |
| Supportive ingredients: | | | | |
| 11. | Amalaki | Dry fruit | *Emblica officinalis* | 8 mg |
| 12. | Hareetaki | Dry fruit | *Terminalia chebula* | 4 mg |
| 13. | Vibhitaki | Dry fruit | *Terminalia bellerica* | 4 mg |
| 14. | Pippali | Dry fruit | *Piper longum* | 4 mg |
| 15. | Maricha | Dry fruit | *Piper nigrum* | 4 mg |
| 16. | Shunthi | Dry rhizome | *Zingiber officinalis* | 4 mg |
| 17. | Bilva | Dry root | *Aegle marmelos* | 2 mg |
| 18. | Agnimantha | Dry root | *Premna mucronata* | 2 mg |
| 19. | Shyonaka | Dry root | *Oroxylum indicum* | 2 mg |
| 20. | Patala | Dry root | *Stereospermum suaveolens* | 2 mg |
| 21. | Gambhari | Dry root | *Gmelina arborea* | 2 mg |
| 22. | Brihati | Dry root | *Solanum indicum* | 2 mg |
| 23. | Kantakari | Dry root | *Solanum xanthocarpum* | 2 mg |
| 24. | Gokshura | Dry fruit | *Tribulus terrestris* | 2 mg |
| 25. | Prishniparni | Dry root | *Uraria picta* | 2 mg |
| 26. | Shalaparni | Dry root | *Desmodium gangeticum* | 2 mg |
| 27. | Brahmi | Dry whole plant | *Bacopa monnieri* | 12 mg |
| 28. | Shankhapushpi | Dry whole plant | *Convolvulus pluricaulis* | 4 mg |
| 29. | Kapikacchu | Dry seeds | *Mucuna pruriens* | 4 mg |
| 30. | Jatamamsi | Dry Rhizome | *Nardostachys jatamansi* | 10 mg |
| 31. | Sarpagandha | Dry root | *Rauwolfia serpentina* | 5 mg |
| 32. | Ashwagandha | Dry root | *Withania somnifera* | 10 mg |
| 33. | Vacha | Dry rhizome | *Acorus calamus* | 4 mg |
| 34. | Shveta Chandana | Dry heartwood | *Santalum album* | 4 mg |
| 35. | Rakta Chandana | Dry heartwood | *Pterocarpus santalinus* | 1 mg |
| 36. | Yashtimadhu | Dry root | *Glycyrrhiza glabra* | 1 mg |
| 37. | Pushkaramoola | Dry root | *Inula racemosa* | 10 mg |
| 38. | Bala | Dry root | *Sida cordifolia* | 1 mg |
| 39. | Tvak | Dry stem bark | *Cinnamomum zeylanica* | 1 mg |
| 40. | Ela | Dry root | *Elettaria cardamomum* | 1 mg |
| 41. | Tulasi | Dry leaves | *Ocimum sanctum* | 1 mg |
| 42. | Guduchi | Dry stem | *Tinospora cordifolia* | 1 mg |
| 43. | Usheera | Dry root | *Vetiveria zizanioides* | 1 mg |
| 44. | Sariva | Dry root | *Hemidesmus indicus* | 1 mg |
| 45. | Rasna | Dry root | *Pluchea lanceolata* | 1 mg |
| 46. | Aragwadha | Dry stem bark | *Cassia fistula* | 1 mg |
| 47. | Padmaka | Dry heartwood | *Prunus cerasoides* | 1 mg |
| 48. | Manjishtha | Dry root | *Rubia cordifolia* | 1 mg |
| 49. | Eranda | Dry leaves | *Ricinus communis* | 1 mg |
| 50. | Nagakesara | Stamens | *Mesua ferrea* | 1 mg |
| 51. | Shilajit | fossil resin | *Asphaltum punjabianum* | 14 mg |
| 52. | Guggulu | oleo-gum-resin | *Commophora mukul* | 10 mg |

TABLE 1-continued

Each 500 mg tablet includes:

| NO. | SANSKRIT NAME | PART USED | SCIENTIFIC NAME | QUANTITY |
|---|---|---|---|---|
| 53. | Mukta shukti bhasma | Incinerated marine mineral | Incinerated pearl oyster (calcium carbonate) | 4 mg |
| 54. | Swarna makshika bhasma | Incinerated ore | Incinerated Copper pyrite | 1 mg |
| 55. | Rajata bhasma | Incinerated metal | Incinerated silver | 1 mg |
| 56. | Pravala bhasma | Incinerated marine mineral | Incinerated coral (calcium carbonate) | 1 mg |
| 57. | Rasasindura | Sublimed mercury sulphide | Red sulphide of mercury | 1 mg |
| 58. | Shringa bhasma | Incinerated animal product | Incinerated Hart's horn | 1 mg |
| 59. | Yashada bhasma | Incinerated metal | Incinerated zinc | 1 mg |
| 60. | Vanga bhasma | Incinerated metal | Incinerated tin | 1 mg |
| 61. | Shankha bhasma | Incinerated marine mineral | Incinerated conch shell (calcium carbonate) | 1 mg |
| 62. | Loha bhasma | Incinerated metal | Incinerated Iron | 5 mg |
| 63. | Abhraka bhasma | Incinerated mineral | Incinerated mica | 5 mg |
| 64. | Tamra bhasma | Incinerated metal | Incinerated copper | 4 mg |
| 65. | Mandura bhasma | Incinerated iron rust | Ferri oxidum precipitatum fuscum | 4 mg |
| 66. | Excipient | Gum | Gum *acacia* | 50 mg |

Embodiments of the disclosed composition in tablet form were analyzed for parameters including physicochemical properties such as Tablet hardness, loss on drying, assay, disintegration time, ash value, etc. and the results were noted. Table 2 depicts the results of the analysis of physicochemical properties of the disclosed composition. In an embodiment, the disclosed composition in tablet form have the characteristics as depicted in Table 2. It will be apparent to those skilled in the art that many modifications, both to materials and methods, may be practiced without departing from the scope of the present invention.

TABLE 2

| TEST PARAMETERS | SPECIFICATIONS |
|---|---|
| Description | Dark brown colored biconvex discs |
| Identification | Positive for Iron, Calcium, silver |
| Average weight | 500 mg ± 12.5 mg |
| Uniformity of weight | ±2.5% of actual average weight |
| Tablet hardness | 4.3 kg/cm$^2$ |
| Loss on drying | 3.68% w/w |
| Methanol soluble extractive | 28.81% w/v |
| Chloroform soluble extractive | 7.0% w/v |
| Ash value | 17.44% w/w |
| Average Disintegration time | 18 minutes |
| ASSAY | Each tablet contains, Iron - 2.84 mg, Calcium - 7.76 mg, silver - 2.42 mg. TLC of alcoholic extract of the drug on silica gel 'G' plate using Toluene:Ethyl acetate (9:1) shows under U.V. light (366 nm), eight spots a Rf. 0.04 (yellow), 0.12 (light green), 0.25 (green), 0.31 (light green), 0.36 (light green), 0.53 (light green), 0.65 (green) and 0.97 (blue). |

Method

Disclosed herein are embodiments of a method of preparing the herbal composition. In an embodiment, the method includes, levigating a mixture of at least one bhasma, Rasasindura, Guggulu and Shilajit in a grinder to obtain a levigated mixture;

adding herbs into said levigated mixture and grinding; and
adding grinding decoction while continuing grinding to obtain a ground mass.

In an embodiment, the method of preparation further includes mixing the obtained ground mass with a suitable excipient and grinding to obtain a homogenous mass. Further, in some embodiments, the obtained homogenous mass may further be processed by methods known in the field to obtain oral dosage forms. In an embodiment, the obtained homogenous mass is subjected to drying, wet granulation and punching. In an embodiment, the homogenous mass is subjected to drying at a temperature of about 50 to 70 degrees Celsius. In an embodiment, the drying is performed in a hot air oven at 60 degrees Celsius. Wet granulation may be performed by methods generally known in the field. In an embodiment, said punching is performed to obtain the disclosed composition in 500 mg tablet form. All raw materials such as herbs and minerals instrumental in the various embodiments herein are of genuine purity and standards whose identity and quality are confirmed by traditional experts. The raw materials instrumental in the various embodiments herein are subjected to appropriate cleaning procedures that are considered standard and acceptable in the field. In an embodiment, the raw materials such as herbs and minerals are subjected to cleaning with potable mineral water prior to its use.

Levigating:

In the various embodiments disclosed herein, levigation of said mixture comprising at least one bhasma, Rasasindura, Guggulu and Shilajit, may be performed by methods generally known in the field. In an embodiment, said levigation is performed by grinding said mixture of at least one bhasma, Rasasindura, Guggulu and Shilajit in a grinder to obtain a levigated mixture. In an embodiment, levigation is performed until a homogenous mixture is obtained. In an embodiment, levigation is performed for a duration of about 1 to 4 hours. In an embodiment, levigation is performed for 3 hours. The mixture of bhasma, Rasasindura, Guggulu and Shilajit instrumental in the embodiments herein may be in a form that facilitates levigation. In an embodiment, said mixture of bhasmas, Guggulu and Shilajit is in a semi-solid form. The bhasmas provided in the mixture for levigation is selected from the group consisting of Mukta shukti bhasma, Swarna makshika bhasma, Rajata bhasma, Pravala bhasma, Shringa bhasma, Yashada bhasma, Vanga bhasma, Shankha bhasma, Loha bhasma, Abhraka bhasma, Tamra bhasma and Mandura bhasma. In an embodiment, the mixture for levigation includes Mukta shukti bhasma, Swarna makshika bhasma, Rajata bhasma, Pravala bhasma, Shringa bhasma, Yashada bhasma, Vanga bhasma, Shankha bhasma, Loha bhasma, Abhraka bhasma, Tamra bhasma, Mandura bhasma, Rasasindura, Guggulu and Shilajit.

The bhasmas that are used in the various embodiments herein may be prepared by methods that are generally known in the field. In an embodiment, the bhasmas may be prepared by a process comprising the following steps: Shodhana or Purification; Trituration; and Marana or Incineration. In an embodiment, the process for the preparation of bhasmas include selecting a mineral; purifying the mineral; triturating the purified mineral; and incinerating said mineral to obtain bhasma.

Selection of a Mineral:

In an embodiment, said mineral is genuine standard mineral such as calcium carbonate, copper pyrite, silver, zinc, iron, mica, hart's horn, copper and iron rust, whose identity and quality has been confirmed by traditional experts. In an embodiment, the selected mineral is further cleaned with potable mineral water; and dried at a temperature of about 40-50 degree Celsius. Drying of the mineral in the various embodiments herein may be achieved by drying in a hot air oven at a temperature of about 50 degree Celsius; or by exposure to sunlight.

Purification of Mineral:

The purification (also referred to as Shodhana) of the mineral may be performed by generally known methods in the field such as triturating, quenching, boiling, etc. In an embodiment, said purification of mineral includes general purification (also referred to as Samanya shodhana) and Special purification (also referred to as Vishesha shodhana). In another embodiment, purification may be a single step process involving boiling, quenching or trituration.

Trituration of Purified Mineral:

Trituration of the mineral may be performed by methods generally known in the field. In an embodiment, trituration is performed by grinding the mineral with an herbal decoction. In another embodiment, trituration is performed by grinding the mineral with herbal juice. The herbal decoction or herbal juice includes any herbal decoction/juice that is generally known to be used for triturating in the preparation of bhasmas such as Triphala, Lemon juice, etc. In yet another embodiment, trituration is performed by grinding the mineral with Gomutra (cow's urine). In an embodiment, trituration of the mineral includes grinding said mineral until a homogenous mixture having reduced particle size is obtained.

Incineration:

Incineration of the mineral may be performed by methods generally known in the field. In an embodiment, said incineration of mineral includes preparing discs of the mineral; and subjecting said discs to a specific quantum and pattern of heat to obtain incinerated mineral powder or bhasma. In an embodiment, said discs have a thickness of about 0.5 cm thickness and a diameter of about 2.5 cm. The prepared discs may further be dried at a temperature of about 40-50 degree Celsius. The discs may be exposed to sunlight or exposed to a temperature of about 50 degrees Celsius in a hot air oven. The discs of mineral are further subjected to heat by sealing inside a capsule made using earthen saucers also known as the puta system of heating which includes preparation of Sharava Samputa and heating in at least one of Gaja puta, Ardha Gaja puta, Kukkuta puta, Laghu puta, etc. The incinerated mineral powder is further powdered and used as bhasma. In an embodiment, the incinerated mineral powder may be subjected to repeated cycles of trituration and incineration in order to obtain a bhasma. In an embodiment, the procedure may be repeated for about 7 to 30 times in order to obtain bhasma. The various bhasmas, according to the embodiments disclosed herein may be prepared by methods generally known in the field. In some embodiments, the method of preparation may be as disclosed hereunder.

Mukta Shukti Bhasma:

The mineral or starting material used in the preparation of Mukta shukti bhasma includes Pearl oyster. The starting material is purified, triturated and incinerated to obtain Muktashukti bhasma. The process of preparing Muktashukti bhasma includes cleaning and drying the mineral, purifying mineral, incinerating, triturating the mineral, and incinerating by puta system to obtain a powder or bhasma. The trituration and incineration process of the obtained powder is further repeated in many cycles to obtain Muktashukti Bhasma. In an embodiment, the obtained powder is triturated and incinerated for 2 cycles in order to obtain Muktashukti Bhasma. The purification of the mineral includes boiling the mineral in Kanjika (also known as sour gruel, a rice-based ayurvedic fermented product) for a period of about 3 to 6 hours. The mineral is further then dried at a temperature of about 60 to 70 degree Celsius. The purified mineral is subjected to puta system of incineration. The incinerated mineral is then triturated with juice of *Aloe vera* and incinerated again, to obtain a powder or bhasma.

Swarna Makshika Bhasma:

The mineral or starting material used in the preparation of Swarna makshika bhasma includes Swarna Makshika (a chalcopyrite). The starting material is purified, triturated and incinerated to obtain Swarna makshika bhasma. The process of preparation of Swarna makshika bhasma includes cleaning and drying the mineral, purifying said mineral, triturating, and incinerating the mineral by puta system to obtain a powder or bhasma. The trituration and incineration process of the obtained powder may further be repeated in many cycles to obtain Swarna makshika bhasma. In an embodiment, the obtained powder is triturated and incinerated in 10 cycles in order to obtain Swarna makshika bhasma. The purification of the mineral includes mixing with rock salt and lemon juice, and heating until partially oxidized into a reddish powder. The purified mineral is then triturated with lemon juice.

Rajata Bhasma:

The mineral or starting material used in the preparation of Rajata bhasma comprises of silver foil. The starting material is purified, triturated and incinerated to obtain Rajata Bhasma. The process of preparation of Rajata bhasma includes cleaning and drying the mineral, purifying said mineral, triturating the purified mineral with herbal decoction and/or herbal juices, and incinerating by puta system to obtain a powder or bhasma. The obtained powder is subjected to the puta system of incineration by generally known methods. The trituration and incineration process of the obtained powder may further be repeated in many cycles to obtain Rajata bhasma. In an embodiment, the obtained powder is triturated and incinerated in 7 cycles in order to obtain Rajata bhasma. The purification step includes heating the mineral and quenching in at least one of the following: sesame oil, buttermilk, cow urine, sour gruel and decoction of *Dolichos biflorus*. The mineral is heated and quenched seven times in each of the liquids separately, and dried. The purification step also includes heating and quenching the mineral in fresh juice of *Sesbania grandiflora* leaves. The heating and quenching steps are repeated seven times to obtain purified mineral. The purified mineral is then triturated with equal quantity of Mercury to obtain an amalgam. The triturated mixture is further triturated with lemon juice by adding purified Sulphur and Manahshila (also known as Realgar). In an embodiment, purified Sulphur and Manahshila (also known as Realgar) is added to the mineral in equal quantities and triturated with lemon juice.

Pravala Bhasma:

The mineral or starting material used in the preparation of Pravala bhasma in the various embodiments herein comprises Coral. The starting material is further purified, triturated and incinerated to obtain Pravala bhasma. In an embodiment, the process of preparation of Pravala bhasma includes cleaning and drying the mineral, purifying said mineral, triturating the purified mineral with herbal decoction and/or herbal juices, and incinerating by puta system to obtain a powder or bhasma. The obtained powder is subjected to the puta system of incineration by generally known methods. The trituration and incineration process of the obtained powder may further be repeated in many cycles to obtain Pravala bhasma. In an embodiment, the obtained powder is triturated and incinerated in 3 cycles in order to obtain Pravala bhasma. The step of purification includes boiling the mineral in alkaline solution of Barilla. The purified mineral is then incinerated by puta system. The incinerated mineral is cooled and subjected to trituration. The mineral is then triturated with herbal decoction and/or herbal juices. The herbal juice used in the preparation of Pravala Bhasma includes *Aloe vera, Asparagus racemosus, Sesbania sesban* and Cow milk. Table 3 depicts the ingredients used in trituration in preparing Pravala Bhasma.

TABLE 3

Herbal juice used in trituration in preparing Pravala Bhasma includes the following:
Juice of following:

| 1. | Kumari fresh leaves | *Aloe vera* | 1 part |
| 2. | Shatavari fresh root | *Asparagus racemosus* | 1 part |
| 3. | Jayanti fresh leaves | *Sesbania sesban* | 1 part |
| 4. | Godugdha | Cow milk | 1 part |

Shringa Bhasma:

The mineral or starting material used in the preparation of Shringa bhasma includes Hart's horn. The starting material is further purified, triturated and incinerated to obtain Shringa Bhasma. In an embodiment, the process of preparation of Shringa bhasma includes cleaning and drying the mineral, purifying said mineral, triturating the purified mineral, and incinerating by puta system to obtain a powder or bhasma. The trituration and incineration process of the obtained powder may further be repeated in many cycles to obtain Shringa Bhasma. In an embodiment, the obtained powder is triturated and incinerated for 3 cycles in order to obtain Shringa Bhasma. The purification process includes boiling the mineral in water and drying. The mineral is further burnt directly on fire, preferably cow dung fueled fire) and powdered. The purified mineral is then triturated with latex from plant *Calotropis procera*.

Yashada Bhasma:

Yashada bhasma may be prepared by methods generally known in the field. The mineral or starting material used in the preparation of bhasma in the various embodiments herein includes Zinc. The starting material is further purified, triturated and incinerated to obtain Yashada Bhasma. The process of preparation of Yashada bhasma includes cleaning and drying the mineral, purifying said mineral, mixing of mineral with purified mercury (also referred to as Shuddha Parada), triturating the purified mineral, and incinerating by puta system to obtain a powder or bhasma. In an embodiment, said purification of the mineral includes melting the mineral, and pouring in lime water. In an embodiment, the purification step may be repeated seven times to obtain purified mineral. In an embodiment, said mixing includes melting purified mineral and adding Shuddha Parada of equal quantity. In an embodiment, the mixture of mineral and Shuddha Parada is triturated to obtain an Amalgam. The obtained Amalgam is further washed with lemon juice and added to purified Sulphur of equal quantity. In an embodiment, the mixture is further triturated to obtain a black powder.

Vanga Bhasma:

The mineral or starting material used in the preparation of Vanga bhasma includes Tin. The starting material is further purified, triturated and incinerated to obtain Vanga Bhasma. In an embodiment, the process of preparation of Vanga bhasma includes cleaning and drying the mineral, purifying said mineral, triturating with herbal decoction and/or herbal juices, and incinerating by puta system to obtain a powder or bhasma. The obtained powder is subjected to the puta system of incineration by generally known methods. The trituration and incineration process of the obtained powder may further be repeated in many cycles to obtain Vanga Bhasma. In an embodiment, the obtained powder is triturated and incinerated for 16 cycles in order to obtain Vanga Bhasma. The purification step includes melting the mineral and pouring in lime water. In an embodiment, the purification step is repeated seven times to obtain purified mineral. The mineral may further be treated with green *Achyranthes aspera*. In an embodiment, poling of the mineral is performed with green *Achyranthes aspera* to get a partially oxidized powder which is used for trituration. The herbal decoction/juice used in the preparation of Vanga bhasma includes decoction of at least one of the following herbs: *Aloe vera* and *Vitex negundo*. Table 4 depicts the ingredients of the herbal juice used in the preparation of Vanga bhasma

TABLE 4

Herbal juice used for trituration in the preparation of Vanga Bhasma.
Juice of following herbs:

| 1. | Kumari fresh leaves | *Aloe vera* | 1 part |
| 2. | Nirgundi fresh leaves | *Vitex negundo* | 1 part |

Loha Bhasma:

Loha bhasma may be prepared by methods generally known in the field. The mineral or starting material used in the preparation of Loha bhasma in the various embodiments herein include Steel iron, (also referred to as "Loha"). The starting material is further purified, triturated and incinerated to obtain Loha Bhasma. In an embodiment, the process of preparation of Loha bhasma includes cleaning and drying the mineral, purifying said mineral, triturating with herbal decoction and/or herbal juices, and incinerating by puta system to obtain a powder or bhasma. The obtained powder is subjected to the puta system of incineration by generally known methods. The obtained powder may further be subjected to repeated cycles of trituration and incineration step to obtain Loha Bhasma. In an embodiment, the obtained powder is triturated and incinerated for 30 cycles in order to obtain Loha Bhasma. The purification process includes quenching the mineral in Triphala decoction. The herbal decoction used in the trituration process of Loha bhasma includes a decoction of at least one of the following ingredients: *Emblica officinalis, Terminalia chebula, Terminalia bellerica, Crataeva nurvala, Boerhavia diffua, Bauhinia variegate* and Cow urine. Table 5 depicts the ingredients of the herbal decoction used in the preparation of Loha bhasma.

TABLE 5

Herbal decoction used for trituration in preparing Loha Bhasma.
Decoction of following herbs:

| | | | |
|---|---|---|---|
| 1. | Amalaki | *Emblica officinalis* | 1 part |
| 2. | Hareetaki | *Terminalia chebula* | 1 part |
| 3. | Vibheetaki | *Terminalia bellerica* | 1 part |
| 4. | Varuna | *Crataeva nurvala* | 1 part |
| 5. | Punarnava | *Boerhavia diffua* | 1 part |
| 6. | Kanchanara | *Bauhinia variegata* | 1 part |
| 7. | Gomutra | Cow urine | 48 parts |
| 8. | Jala | Water | 48 parts |
| | Avashesha (Reduced to) | | ⅛ part of liquid |

In another embodiment, the herbal juice used for triturating includes *Boerhavia diffusa* and *Eclipta alba* such as that in the preparation of Loha bhasma. Table 6 illustrates the list of herbs for the herbal juice used in the preparation of Loha bhasma.

TABLE 6

Herbal juice used for trituration while preparing Loha bhasma
Juice of following herbs:

| | | | |
|---|---|---|---|
| 1. | Punarnava fresh plant | *Boerhavia diffusa* | 1 part |
| 2. | Bhringaraja fresh plant | *Eclipta alba* | 1 part |

Abhraka Bhasma:

The mineral or starting material used in the preparation of Abhraka bhasma includes Mica. The starting material is further purified, triturated and incinerated to obtain Abhraka Bhasma. In an embodiment, the process of preparation of Abhraka bhasma includes cleaning and drying the mineral, purifying said mineral, triturating with herbal decoction and/or herbal juice, and incinerating by puta system to obtain a powder or bhasma. The obtained powder is subjected to the puta system of incineration by generally known methods. The trituration and incineration process of the obtained powder may further be repeated in many cycles to obtain Abhraka Bhasma. In an embodiment, the obtained powder is triturated and incinerated for 30 cycles in order to obtain Abhraka Bhasma. The purification step includes quenching the mineral in Cow's milk. The purified mineral may further be bundled in woolen cloth, dipped in water and squeezed to obtain microfine particles. The herbal decoction used in the preparation of Abhraka bhasma includes at least one of the following ingredients: *Emblica officinalis, Terminalia chebula, Terminalia bellerica, Cyperus rotundus, Ficus benghalensis* and *Curcuma longa*. Table 7 illustrates the list of ingredients for the herbal decoction used in the preparation of Abhraka bhasma.

TABLE 7

Herbal decoction used for trituration in preparing Abhraka bhasma
Decoction of following herbs:

| | | | |
|---|---|---|---|
| 1. | Amalaki dried fruit | *Emblica officinalis* | 1 part |
| 2. | Hareetaki dried fruit | *Terminalia chebula* | 1 part |

TABLE 7-continued

Herbal decoction used for trituration in preparing Abhraka bhasma
Decoction of following herbs:

| | | | |
|---|---|---|---|
| 3. | Vibheetaki dried fruit | *Terminalia bellerica* | 1 part |
| 4. | Musta dried rhizome | *Cyperus rotundus* | 1 part |
| 5. | Vata dried root bark | *Ficus bengalensis* | 1 part |
| 6. | Haridra dried rhizome | *Curcuma longa* | 1 part |
| 7. | Jala | Water | 96 parts |
| | Avashesha (Reduced to) | | ⅛ part of liquid |

The herbal juice used in the preparation of Abhraka bhasma includes at least one of the following ingredients: *Cassia occidentalis, Cynodon dactylon, Adhatoda vasica, Emblica officinalis, Alternanthera sessilis, Amaranthus spinosus, Ricinus communis, Solanum nigrum, Eclipta alba* and *Punica granatum*. Table 8 illustrates the list of herbs for the herbal juice used in the preparation of Abhraka bhasma.

TABLE 8

Herbal juice used for trituration while preparing Abhraka bhasma
Juice of following herbs:

| | | | |
|---|---|---|---|
| 1. | Kasamarda fresh leaves | *Cassia occidentalis* | 1 part |
| 2. | Durva fresh plant | *Cynodon dactylon* | 1 part |
| 3. | Vasa fresh leaves | *Adhatoda vasica* | 1 part |
| 4. | Amalaki fresh fruit | *Emblica officinalis* | 1 part |
| 5. | Matsyakshi fresh plant | *Alternanthera sessilis* | 1 part |
| 6. | Tanduleeyaka fresh plant | *Amaranthus spinosus* | 1 part |
| 7. | Eranda fresh leaves | *Ricinus communis* | 1 part |
| 8. | Kakamachi fresh leaves | *Solanum nigrum* | 1 part |
| 9. | Bhringaraja fresh plant | *Eclipta alba* | 1 part |
| 10 | Dadima fresh leaves | *Punica granatum* | 1 part |

Mandura Bhasma:

The mineral or starting material used in the preparation of Mandura bhasma includes iron rust, preferable iron rust (oxidized iron) which is at least 60 years, (also referred to as "Mandura"). The starting material is purified, triturated and incinerated to obtain Mandura Bhasma. In an embodiment, the process for the preparation of Mandura bhasma includes cleaning and drying Mandura, purifying said Mandura by Samanya Shodhana (General purification) and Vishesha Shodhana, (Special purification), exposing to sun light by Bhanupaka, triturating with Triphala decoction and Cow's urine, and incinerating by puta system to obtain a powder or bhasma. The mineral is subjected to the puta system of incineration by generally known methods. The obtained powder may further be triturated with Triphala decoction and Cow's urine and incinerated again to obtain bhasma. The trituration and incineration process may further be repeated in repeated cycles to obtain a Bhasma. In an embodiment, the obtained powder is triturated and incinerated for 30 cycles in order to obtain Mandura Bhasma. Further, Samanya Shodhana, Vishesha Shodhana and Bhanupaka of the mineral may be performed by methods generally known in the field. The step of Samanya Shodhana includes heating the mineral until it turns red hot followed by dipping in 5 different liquid media, separately, such as sesame oil, butter milk, cow urine, Kanji (also known as "Kanjika" or sour medicated rice gruel) and Horse gram decoction. In an embodiment, Samanya Shodhana is repeated 7 times in each liquid. The step of Vishesha Shodhana includes heating the mineral until red hot and then immersing the mineral in Triphala decoction.

Bhanupaka of mineral includes adding Triphala decoction to purified Mandura, and exposing it to sunlight until complete evaporation occurs. In an embodiment, Bhanupaka is repeated 7 times.

Shankha Bhasma:

The mineral or starting material used in the preparation of Shankha bhasma is seashell. One example of such starting material is Conch shells (also known as Shankha). The starting material is purified, triturated and incinerated to obtain Shankha Bhasma. The process of preparation of Shankha bhasma includes cleaning and drying the mineral, purifying said mineral, incineration, triturating, and incinerating by puta system to obtain a powder or bhasma. The obtained powder is subjected to the puta system of incineration by generally known methods. The trituration and incineration process of the obtained powder may further be repeated in many cycles to obtain Shankha bhasma. In an embodiment, the obtained powder is triturated and incinerated for 4 cycles in order to obtain Shankha Bhasma. The purification step includes boiling the mineral in Kanjika for about 1 to 3 hours, preferably the mineral is bundled in a cloth. The mineral is then washed and dried at about 40 to 60 degrees Celsius. The purified mineral is then subjected to incineration by puta system. The mineral is then triturated with juice of *Aloe vera* leaves.

Tamra Bhasma:

The mineral or starting material used in the preparation of Tamra bhasma is copper. One example of the starting material is Copper foil. The starting material is purified, triturated and incinerated to obtain Tamra Bhasma. In an embodiment, the process of preparation of Tamra bhasma includes cleaning and drying the mineral, purifying said mineral, incineration, triturating the mineral, and incinerating by puta system to obtain a powder or bhasma. The obtained powder is subjected to the puta system of incineration by generally known methods. The trituration and incineration process of the obtained powder may be repeated in many cycles to obtain Tamra bhasma. In an embodiment, the obtained powder is triturated and incinerated for 10 cycles in order to obtain Tamra Bhasma. The purification step includes heating the mineral and quenching in at least one of the following: sesame oil, buttermilk, cow urine, sour gruel and decoction of *Dolichos biflorus*. The mineral is heated and quenched seven times in each of the liquids separately, and dried. In an embodiment, the purification includes applying a paste of Rock salt (also known as Saindhava salt) and lemon juice, on the mineral, and drying at a temperature of about 40 to 60 degree Celsius. The mineral is further heated and quenched in fresh juice of *Vitex negundo* leaves, in seven repeated cycles. The purification includes applying a paste of black sulphide of mercury and lemon juice on the mineral and drying at a temperature of about 40 to 60 degree Celsius. The mineral is then incinerated. The trituration of mineral is performed with lemon juice and Kajjali (black sulphide of mercury) taken in equal amounts.

Adding Herbs to Levigated Mixture and Grinding:

In the various embodiments disclosed herein, this step includes adding herbs to the levigated mixture and mixing to obtain a homogenous mass. In an embodiment, mixing is performed in a grinder, such that a homogenous mass is obtained. The herbs that are mixed with the levigated mixture includes finely powdered herbs that are instrumental in the composition disclosed in the various embodiments herein. In an embodiment, the herbs include whole plant of *Phyllanthus niruri*, whole plant of *Eclipta alba*, roots of *Boerhavia diffusa*, whole plant of *Swertia chirata*, fruit of *Embelia ribes*, heartwood of *Acacia catechu*, root of *Plumbago zeylanica*, stem bark of *Terminalia arjuna*, tuber of *Pueraria tuberosa*, root of *Picrorhiza kurroa* and resin of *Commiphora mukul*. In another embodiment, the herbs include dried and finely powdered whole plant of *Phyllanthus niruri*, whole plant of *Eclipta alba*, roots of *Boerhavia diffusa*, whole plant of *Swertia chirata*, fruit of *Embelia ribes*, heartwood of *Acacia catechu*, root of *Plumbago zeylanica*, stem bark of *Terminalia arjuna*, tuber of *Pueraria tuberosa*, root of *Picrorhiza kurroa*, fruit of *Emblica officinalis*, fruit of *Terminalia chebula*, fruit of *Terminalia bellerica*, fruit of *Piper longum*, fruit of fruit of *Tribulus terrestris*, fruit of *Piper nigrum*, rhizome of *Zingiber officinalis*, rhizome of *Acorus calamus*, rhizome of *Nardostachys jatamansi*, root of *Aegle marmelos*, root of *Premna mucronata*, root of *Glycyrrhiza glabra*, root of *Inula racemosa*, root of *Sida cordifolia*, root of *Rauwolfia serpentina*, root of *Rubia cordifolia*, root of *Vetiveria zizanioides*, root of *Hemidesmus indicus*, root of *Pluchea lanceolata*, root of *Elettaria cardamomum*, root of *Withania somnifera*, root of *Oroxylum indicum*, root of *Stereospermum suaveolens*, root of *Uraria picta*, root of *Desmodium gangeticum*, root of *Gmelina arborea*, root of *Solanum indicum*, root of *Solanum xanthocarpum*, whole plant of *Bacopa monnieri*, whole plant of *Convolvulus pluricaulis*, seeds of *Mucuna pruriens*, heartwood of *Santalum album*, heartwood of *Prunus cerasoides*, heartwood of *Pterocarpus santalinus*, stem bark of *Cinnamomum zeylanica*, stem bark of *Cassia fistula*, leaves of *Ocimum sanctum*, leaves of *Ricinus communis*, stem of *Tinospora cordifolia*, stamen of *Mesua ferrea* and resin of *Commiphora mukul*. In an embodiment, finely powdered herbs may be obtained by powdering and sieving the dry herb or herb components through 80 mesh screen. In the various embodiments disclosed herein, grinding may be performed by methods generally known in the field. In an embodiment, grinding is performed in a grinder at about 80-150 rpm to obtain an herbal mixture.

Adding Grinding Decoction while Continuing Grinding to Obtain a Ground Mass:

In the various embodiments disclosed herein, the step of adding Grinding decoction includes mixing said Grinding decoction to the herbal mixture obtained from the earlier step. Once the Grinding decoction is added and mixed to the herbal mixture, grinding is continued for a duration of about 1 to 3 days at about 100-150 rpm to obtain an embodiment of the disclosed composition. In an embodiment, said grinding is continued for a duration of 72 hours.

The grinding decoction disclosed in the various embodiments herein is a decoction of certain herbs (also referred to as "Grinding ingredients"). Table 9 provides a list of Grinding ingredients. In an embodiment, the Grinding decoction includes a decoction of at least one herb selected from a group consisting of *Phyllanthus niruri, Eclipta alba, Asparagus racemosus, Aegle marmelos, Premna mucronata, Oroxylum indicum, Stereospermum suaveolens, Gmelina arborea, Solanum indicum, Solanum xanthocarpum, Tribulus terrestris, Uraria picta, Desmodium gangeticum, Aloe vera, Azadirachta indica, Tinospora cordifolia, Bacopa monneri, Acorus calamus, Celastrus paniculatus, Nardostachys jatamansi* and *Rauwolfia serpentina*. In another embodiment, the Grinding decoction includes a decoction of at least one herb selected from a group consisting of *Phyllanthus niruri* and *Eclipta alba*. The grinding ingredients that are used in the various embodiments herein may comprise of the herbs as a whole or in parts such as leaves, roots, stem, fruits, seeds, etc. The grinding ingredients that are used may comprise of herbs in dry or fresh form. In an embodiment, said grinding ingredients include coarsely powdered form of herbs that is sieved through a 10-mesh screen.

In an embodiment, the method of preparation of grinding decoction further includes, soaking the grinding herbs i.e. fresh whole plant of *Phyllanthus niruri*, fresh whole plant of *Eclipta alba*, dried roots of *Asparagus racemosus*, dried roots of *Aegle marmelos*, dried roots of *Premna mucronata*, dried roots of *Oroxylum indicum*, dried roots of *Stereospermum suaveolens*, dried roots of *Gmelina arborea*, dried roots of *Solanum indicum*, dried roots of *Solanum xanthocarpum*, dried fruit of *Tribulus terrestris*, dried roots of *Uraria picta*, dried roots of *Desmodium gangeticum*, fresh leaves of *Aloe vera*, fresh leaves of *Azadirachta indica*, fresh stem of *Tinospora cordifolia*, fresh whole plant of *Bacopa monnieri*, dried rhizome of Acorns calamus, dried seeds of *Celastrus paniculatus*, dried rhizome of *Nardostachys jatamansi* and dried root of *Rauwolfia serpentina*; and concentrating by boiling.

In another embodiment, the method of preparation of grinding decoction further includes, soaking the grinding herbs i.e. fresh whole plant of *Phyllanthus niruri* and fresh whole plant of *Eclipta alba*; and concentrating by boiling.

In an embodiment, said soaking may be performed by soaking the grinding herbs in 16 parts of water overnight. In an embodiment, said soaking is performed by soaking 1 part of equal quantities of each of the grinding herbs in 16 parts of water overnight. In a further embodiment, concentrating may be performed by boiling at high temperature, preferably about 80 to 85 degree Celsius, until ⅛th of the liquid remains. Concentration may be confirmed with the help of Brix meter.

forms of the disclosed composition. In an embodiment, the method of preparation further includes drying of the obtained semi solid mass, wet-granulating and punching of the composition to obtain tablets. In another embodiment, said drying of the obtained semi solid mass includes drying at about 60 degree Celsius, preferably in a hot air oven. In another embodiment, said punching is performed to obtain 500 mg tablets. FIG. 1 is a flowchart depicting the preparation of the disclosed composition in the form of fortified tablets.

Treatment

Disclosed herein are embodiments of the method for the treatment and management of addiction and associated complications. The embodiments disclosed herein are instrumental in alleviating withdrawal symptoms associated with addiction such as tremors, headache, restlessness, anxiety, depression, constipation, insomnia, coughing etc. Further, the embodiments of the disclosed composition are also observed to be effective in the treatment and management of complications associated with addiction such as fatty liver, liver cirrhosis, renal disorders, lung disorders etc. The various embodiments herein are also instrumental in alleviating clinical symptoms associated with addiction such as asthenia, easy fatigability, tiredness, nausea, anorexia, abdominal discomfort, abdominal pain, stool frequency and muscle cramps.

In an embodiment, the method includes administering to a patient in need thereof a composition as described in the various embodiments herein. Patients may include any indi-

TABLE 9

List of Grinding ingredients

Decoction of following herbs:

| | | | |
|---|---|---|---|
| 1. Bhumyamalaki fresh whole plant | *Phyllanthus niruri* | 1 | part |
| 2. Bhringaraja fresh whole plant | *Eclipta alba* | 1 | part |
| 3. Shatavari dried root | *Asparagus racemosus* | 1 | part |
| 4. Bilva dried root | *Aegle marmelos* | 1 | part |
| 5. Agnimantha dried root | *Premna mucronata* | 1 | part |
| 6. Shyonaka dried root | *Oroxylum indicum* | 1 | part |
| 7. Patala dried root | *Stereospermum suaveolens* | 1 | part |
| 8. Gambhari dried root | *Gmelina arborea* | 1 | part |
| 9. Brihati dried root | *Solanum indicum* | 1 | part |
| 10. Kantakari dried root | *Solanum xanthocarpum* | 1 | part |
| 11. Gokshura dried fruit | *Tribulus terrestris* | 1 | part |
| 12. Prishniparni dried root | *Uraria picta* | 1 | part |
| 13. Shalaparni dried root | *Desmodium gangeticum* | 1 | part |
| 14. Kumari fresh leaf | *Aloe vera* | 1 | part |
| 15. Nimba fresh leaves | *Azadirachta indica* | 1 | part |
| 16. Guduchi fresh stem | *Tinospora cordifolia* | 1 | part |
| 17. Brahmi fresh whole plant | *Bacopa monnieri* | 1 | part |
| 18. Vacha dried rhizome | *Acorus calamus* | 1 | part |
| 19. Jyotishmati dried seeds | *Celastrus paniculatus* | 1 | part |
| 20. Jatamamsi dried rhizome | *Nardostachys jatamansi* | 1 | part |
| 21. Sarpagandha | *Rauwolfia serpentina* | 1 | part |
| Jala | Water | 336 | parts |
| Avashesha (Reduced to) | | ⅛ | part of water |

The method of preparation of the herbal composition disclosed in the various embodiments herein further includes mixing of excipient to the obtained composition and grinding to obtain a semi solid mass. The excipient may be added to the composition directly or in a dissolved form. In an embodiment, the excipient is added to the composition by dissolving the excipient in the Grinding decoction. In another embodiment, the excipient is gum acacia which is added to the composition by dissolving in the Grinding decoction. The method of preparation may further include various other steps that may be instrumental in processing the obtained composition in order to achieve oral dosage vidual in need of such treatment including ones having an addiction such as alcoholics, smokers etc. Patient also includes any individual having complications associated with addiction such as fatty liver, liver cirrhosis, renal disorders, lung disorders etc. Further, patient includes individuals having clinical symptoms associated with addiction such as asthenia, easy fatigability, tiredness, nausea, anorexia, abdominal discomfort, abdominal pain, stool frequency and muscle cramps. Patient would also include individuals having withdrawal symptoms associated with addiction such as tremors, headache, restlessness, anxiety, depression, constipation, insomnia, coughing etc.

In an embodiment, the method includes administering to a patient a composition having at least one herb, at least one mineral and at least one suitable excipient. In an embodiments, the method includes administering to a patient a composition having *Phyllanthus niruri* (4 to 8 wt. %), *Eclipta alba* (2 to 6 wt. %), *Boerhavia diffusa* (2 to 6 wt. %), *Swertia chirata* (2 to 6 wt. %), *Embelia ribes* (2 to 6 wt. %), *Acacia catechu* (2 to 6 wt. %) and *Pueraria tuberosa* (2 to 6 wt. %), *Plumbago zeylanica* (6 to 10 wt. %), *Terminalia arjuna* (6 to 10 wt. %), *Picrorhiza kurroa* (6 to 10 wt. %), *Commiphora mukul* (≤1 wt. %), *Emblica officinalis* (≤2 wt. %), *Terminalia chebula* (≤2 wt. %), *Terminalia bellerica* (≤2 wt. %), *Piper longum* (≤2 wt. %), *Piper nigrum* (≤2 wt. %), *Zingiber officinalis* (≤2 wt. %), *Aegle marmelos* (≤2 wt. %), *Premna mucronata* (≤2 wt. %), *Oroxylum indicum* (≤2 wt. %), *Stereospermum suaveolens* (≤2 wt. %), *Gmelina arborea* (≤2 wt. %), *Solanum indicum* (≤2 wt. %), *Solanum xanthocarpum* (≤2 wt. %), *Tribulus terrestris* (≤2 wt. %), *Uraria picta* (≤2 wt. %), *Desmodium gangeticum* (≤2 wt. %), *Bacopa monnieri* (≤3 wt. %), *Convolvulus pluricaulis* (≤2 wt. %), *Mucuna pruriens* (≤2 wt. %), *Nardostachys jatamansi* (≤3 wt. %), *Rauwolfia serpentina* (≤2 wt. %), *Withania somnifera* (≤3 wt. %), *Acorus calamus* (≤2 wt. %), *Santalum album* (≤2 wt. %), *Pterocarpus santalinus* (≤2 wt. %), *Glycyrrhiza glabra* (≤2 wt. %), *Inula racemosa* (≤3 wt. %), *Sida cordifolia* (≤2 wt. %), *Cinnamomum zeylanica* (≤2 wt. %), *Elettaria cardamomum* (≤2 wt. %), *Ocimum sanctum* (≤2 wt. %), *Tinospora cordifolia* (≤2 wt. %), *Vetiveria zizanioides* (≤2 wt. %), *Hemidesmus indicus* (≤2 wt. %), *Pluchea lanceolata* (≤2 wt. %), *Cassia fistula* (≤2 wt. %), *Prunus cerasoides* (≤2 wt. %), *Rubia cordifolia* (≤2 wt. %), *Ricinus communis* (≤2 wt. %) and *Mesua ferrea* (≤2 wt. %), Mukta shukti bhasma (≤1 wt. %), Swarna makshika bhasma 1 wt. %), Rajata bhasma 1 wt. %), Pravala bhasma (≤1 wt. %), Shringa bhasma (≤1 wt. %), Yashada bhasma 1 wt. %), Vanga bhasma (≤1 wt. %), Shankha bhasma (≤1 wt. %), Loha bhasma (≤2 wt. %), Abhraka bhasma (≤2 wt. %), Tamra bhasma (≤1 wt. %), Mandura bhasma (≤1 wt. %), Rasasindura (≤1 wt. %), Shilajit (≤3 wt. %) and Gum acacia (8 to 12 wt. %). The disclosed method of treatment may be used as a primary line of treatment or as an adjunct to other treatment methods for addiction.

The patient may be administered a therapeutically effective amount of the embodiments of the disclosed composition. The therapeutically effective amount may vary depending on the patient. In an embodiment, the therapeutically effective amount is 500 to 1000 mg administered one to three times a day. The disclosed embodiments were subjected to acute oral toxicity study according to OECD test guideline 423, Acute Toxic Class Method with modifications.

The study showed that the LD50 cut-off value of Test drug was greater than 2000 mg/kg body weight, p.o and was classified as Category-5 or unclassified based on Globally Harmonized System of Classification and Labelling of Chemicals.

Embodiments of the Disclosed composition (also referred as Test drug) were further evaluated for efficacy (preclinical and clinical studies), as described hereunder by way of examples. Embodiments are further described by reference to the following example by way of illustration only and should not be construed to limit the scope of the claims provided herewith. It will be apparent to those skilled in the art that many modifications, both to materials and methods, may be practiced without departing from the scope of the claims.

Example 1: Preclinical Study

Aim of Study:

The aim of this study was to analyze the effect of Test drug on alcohol-induced mortality and liver lesions in mice.

The Test drug used in the study was solid having stability in 0.5% CMC for a period of 2 hours and partially soluble in water. Test subjects were female swiss albino mice of about 9-10 weeks of age at the start of Dosing. Acclimatization was done for six days under laboratory conditions. Body weight was recorded on day 0 and 6 days of acclimatization. Randomization was performed on last day of acclimatization. Healthy mice were selected and grouped based on body weight. Mice were marked with 0.1% picric acid on body for identification. Animals were grouped and treated as mentioned below after randomization. Table 10 illustrates the grouping and treatment details of subjects.

Experimental Conditions:

Temperature and relative humidity were maintained at a range of 19-25° C. and 30-70%, respectively, and recorded twice a day. Animals were maintained in 12 h light/12 h dark artificial photoperiod throughout the experimental period. Mice were housed in groups with 3 in polypropylene cages (22 L×18B×12 H cm). Cages were covered with stainless steel grid top. Paddy husk was used as bedding material. Soiled cages were changed on alternate days or as and when required. Mice were provided with standard laboratory rodent feed. Reverse osmosis (RO) water was provided ad libitum.

TABLE 10

| No. | Group | Treatment | No. of animals/group | Animal number |
|---|---|---|---|---|
| I | Vehicle control | 0.5% CMC (10 ml/kg, p.o) | 8 | 101-108 |
| II | Positive control | Alcohol in drinking water + 0.5% CMC (10 ml/kg, p.o) | 8 | 201-208 |
| III | Reference control | Alcohol in drinking water + Silymarin (100 g/kg, p.o) | 8 | 301-308 |
| IV | Test | Alcohol in drinking water + Test drug (30 mg/kg, p.o) | 8 | 401-408 |
| V | Test | Alcohol in drinking water + Test drug (100 mg/kg, p.o) | 8 | 501-508 |
| VI | Test control | Test drug (100 mg/kg, p.o) | 8 | 601-608 |

Procedure:

Test drug was suspended in 0.5% carboxy methyl cellulose (CMC) as vehicle. Test drug was freshly prepared in vehicle prior to dosing by trituration. The Test drug was weighed, transferred to mortar and grinded with pestle. A small quantity of the vehicle was added to Test drug and triturated. This was transferred to a measuring cylinder. A small quantity of the vehicle was added to motor again, triturated and transferred to the measuring cylinder. Sufficient quantity of vehicle was added to make up the required volume of composition. The composition prepared was then transferred to motor and again triturated. Following trituration, the composition was transferred to a labelled beaker for dosing. The proposed route of human exposure is oral, hence the Test drug was administered through oral route in mice. The dose volume of the composition was 10 ml/kg body weight.

Induction of Hepatotoxicity:

Alcoholic intoxication was induced using ethanol. Concentration of ethanol was progressively increased in the drinking water viz 10% (v/v) alcohol in the first week, 20% in the second, 30% in the third, and 40% in the fourth week. Animals were treated with vehicle or Test drug simultaneously (10.00 am to 11.00 am) for 28 days. On day 29, the animals were fasted for 4 h and blood samples were collected for biochemical analysis. The animals were then euthanized (ketamine 100 mg/kg, i.p) and liver sample were harvested for histopathological evaluation.

Test Parameters:

Liver function test: Plasma Biochemistry—ALT, AST, ALP, γ-GT and total bilirubin, was analyzed using diagnostic kit (Eg: Spinreact, Spain) in Semi-automatic biochemical analyzer (Eg: Labmate, India).

Histopathology:

Liver collected from mice were fixed in 10% neutral buffered formalin solution, dehydrated in graded alcohol and embedded in paraffin. Paraffin sections of 3-5 micron were mounted on glass slides and counter-stained with Hematoxylin and Eosin (H&E) for light microscopic analysis.

Data Analysis:

Data was expressed as mean±SEM. Mean difference between the groups were analyzed by one-way anova followed by Tukey's multiple comparison test as post hoc. p value≤0.05 was considered as statistically significant.

Figure 2:
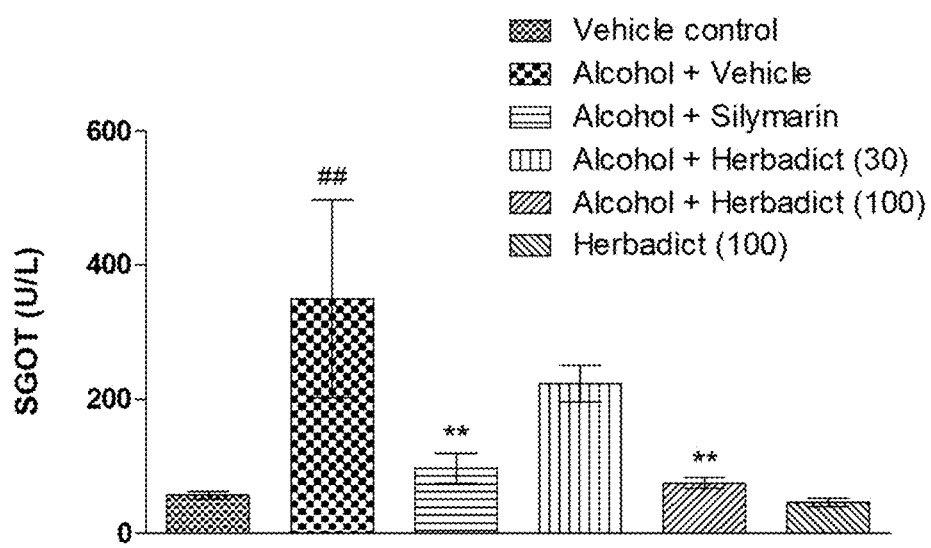
FIG. 2 is a graphical representation depicting the effect of Test drug on plasma serum glutamic-oxaloacetic transaminase (SGOT) activity in alcohol intoxicated mice.
Figure 3:
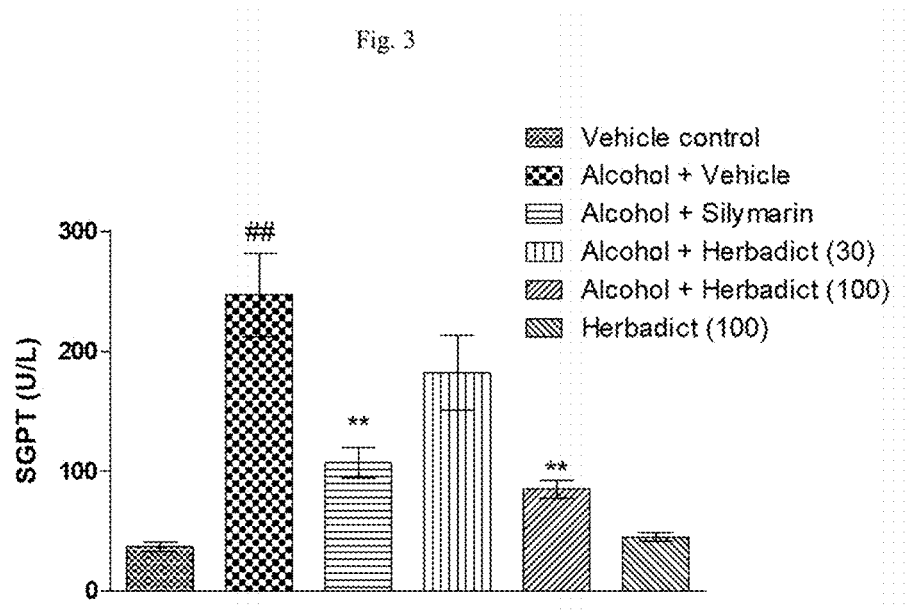
FIG. 3 is a graphical representation depicting the effect of Test drug on plasma Serum glutamic pyruvic transaminase (SGPT) activity in alcohol intoxicated mice.
Figure 4:
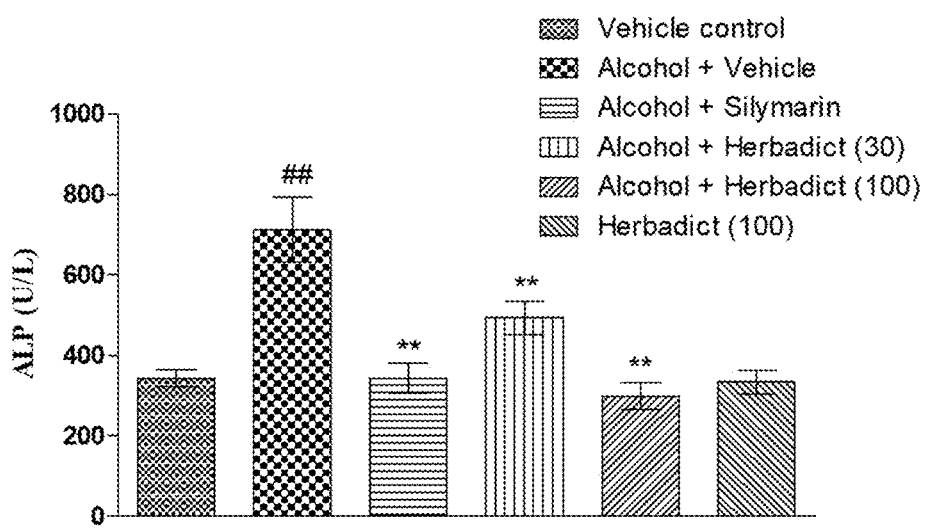
FIG. 4 is a graphical representation depicting the effect of Test drug on plasma Alkaline phosphatase (ALP) activity in alcohol intoxicated mice.
Figure 5:
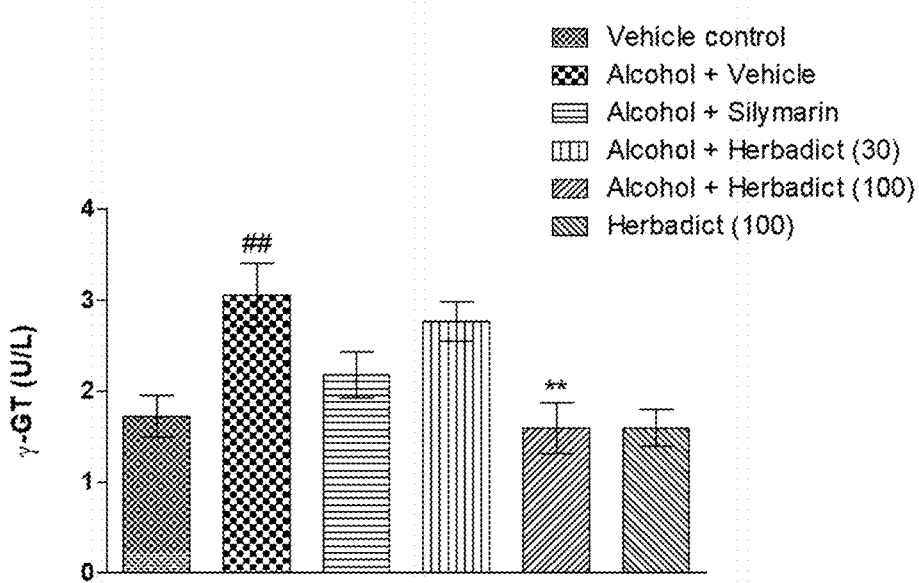
FIG. 5 is a graphical representation depicting the effect of Test drug on plasma γ-GT activity in alcohol intoxicated mice.
Figure 6:
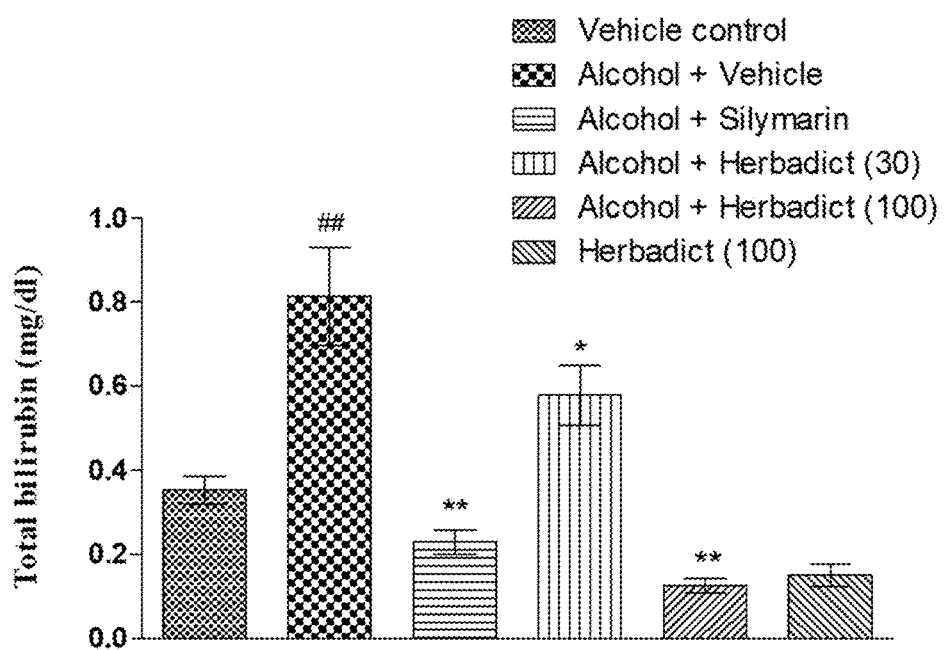
FIG. 6 is a graphical representation depicting the effect of Test drug on total bilirubin content in alcohol intoxicated mice.

Results:

Plasma Biochemistry:

Alcohol intoxicated mice showed significant (p<0.01) increase in SGOT, SGPT, ALP, γ-GT and total bilirubin levels when compared to vehicle control mice. FIG. 2 depicts the effect of Test drug on plasma SGOT activity in alcohol intoxicated mice. FIG. 3 depicts the effect of Test drug on plasma SGPT activity in alcohol intoxicated mice. FIG. 4 depicts the effect of Test drug on plasma Alkaline Phosphatase (ALP) activity in alcohol intoxicated mice. FIG. 5 depicts the effect of Test drug on plasma γ-GT activity in alcohol intoxicated mice. FIG. 6 depicts the effect of Test drug on total Bilirubin content in alcohol intoxicated mice. Treatment with Test drug significantly (p<0.01) decreased SGOT, SGPT and γ-GT at 100 mg/kg when compared to the vehicle treated alcohol intoxicated group. A significant (p<0.01) decrease in ALP was recorded at both 30 and 100 mg/kg doses of Test drug when compared to the vehicle treated alcohol intoxicated group. A dose dependent significant decrease in total bilirubin was observed at 30 and 100 mg/kg of Test drug when compared to vehicle treated alcohol intoxicated group. Effect of Test drug was comparable with that of the reference drug, Silymarin.

Figure 7:
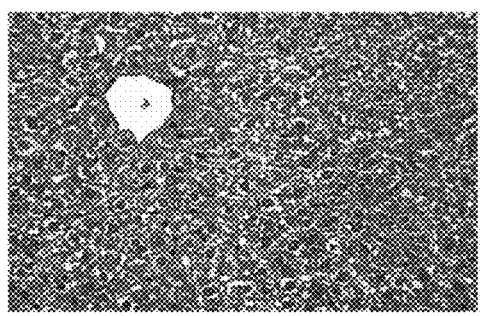
FIG. 7 is pictorial representations of liver sections showing the effect of Test drug in mice of Group I, Group II, Group III, Group IV, Group V and Group VI, according to the embodiments.
Figure 7:
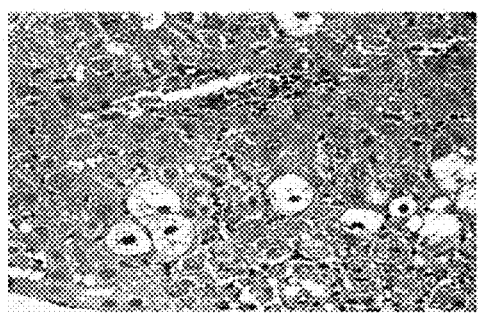
Figure 7:
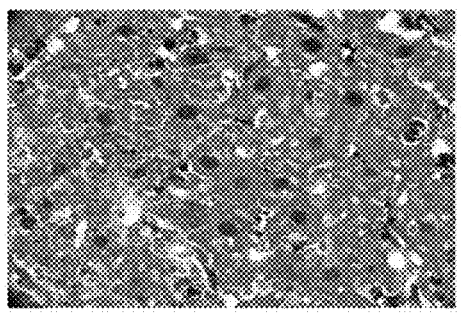
Figure 7:
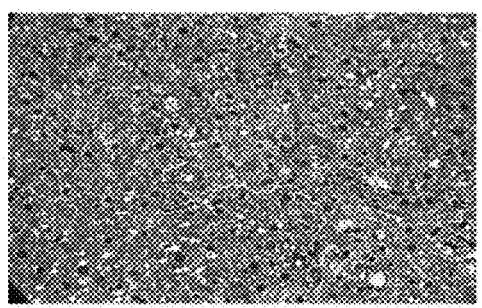
Figure 7:
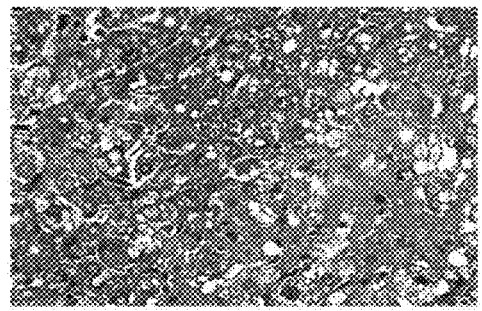
Figure 7:
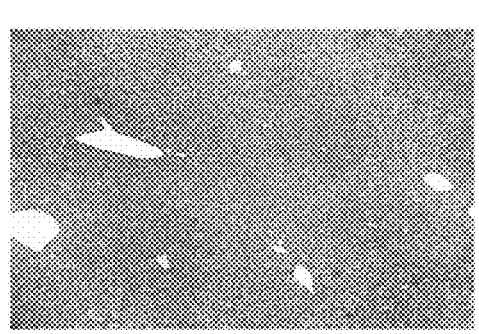

Histopathology:

In Group I or Vehicle control, Liver section showed normal architecture with central vein, hepatocytes radiating from the central veins and the portal triads. In Group II or Positive Control, Liver sections revealed moderate to severe degree of hepatocellular vacuolations multifocal areas of ballooning degeneration of the hepatocytes. Few hepatocytes showed granular cytoplasm. Dilatation of sinusoidal spaces containing erythrocytes was also noticed. Focal areas of perivascular lymphocytic infiltration and centrilobular necrosis. In Group III or Reference control, Liver sections revealed moderate degree of vacuolations within the hepatocytes, mild degree of ballooning degeneration in hepatocytes and mononuclear cells infiltration in the necrotized area. In Group IV or Treatment with Test drug at 30 mg/kg p.o., Liver sections revealed mild degree of hepatocellular vacuolations, minimal degree of ballooning degeneration, absence of sinusoidal dilatation and necrosis. Focal area of restoration of normal parenchyma was evident. In Group V or Pre-treatment with Test drug at 100 mg/kg p.o., Liver sections revealed moderate degree of vacuolations and ballooning degeneration of hepatocytes, focal areas of perivascular infiltration and centrilobular necrosis. In Group VI or Pre-treatment with Livokot at 300 mg/kg p.o., Liver lesions were similar to the positive control. FIG. 7 is a representation of livers sections illustrating the effect of Test drug against alcohol induced hepatic changes in mice.

Conclusion:

Treatment with Test Drug at 30 and 100 mg/kg p.o. showed hepatoprotective effect against alcohol induced damage in mice model.

Example 2: Clinical Study I

Aim of Study:

The aims of this study were as follows: to evaluate the effect of Test drug on alcoholism; and to evaluate the effect of Test drug on alcoholic liver disease Objectives of the Study on Alcoholism:

The objectives were as follows: to evaluate the action of Test drug on withdrawal symptoms; to evaluate the effect of Test drug on alcoholic liver diseases; to observe the effect of Test drug on disturbed sleep; and to assess the effect of Test drug in increasing the will power to withdraw from addiction. The total number of patients studied were 214.

Objectives of the Study on Alcoholic Liver Disease:

The objectives were as follows: to evaluate the efficacy of Test drug tablet in clinical signs and symptoms of alcoholic liver cirrhosis patients; and to evaluate the efficacy of Test drug tablet on liver function test. The total number of patients: 40

Patients and Methods:

Inclusion Criteria:

All patients aged between 28 to 71 years, and suffering from early alcoholic cirrhosis were included in the study. For study on de-addiction, chronic alcoholic addicts with or without alcoholic liver disease but with withdrawal symptoms are included.

Exclusion Criteria:

Patients having evidence of Esophageal varices, Hepatic encephalopathy and Malignant jaundice. Pregnant women were also excluded from the study.

Procedure:

The study was an open, nonrandomized and non-comparative, prospective clinical trial. Patients were informed about the study drug, its effects, duration of the trial, and overall plan of the study. The patients were included in the clinical study only after written informed consent was obtained from each of them, and a witness, independent of the clinical trial, signed the informed consent form. The history was noted by interviewing the patient. Thorough clinical examination and symptomatic evaluation was carried out and the details were noted down in the clinical research proforma. All patients were reviewed every month till the end of treatment, and symptomatic evaluation and clinical examination was done, along with recording the occurrence of any adverse event/s (either reported or observed). Liver function tests, hemogram and other biochemical tests were done at baseline and at the end of the study after 6 months. Patients were advised to take Test drug tablet at a dose of 2 tablets (500 mg×02) twice a day, for 6 months.

Table 11 illustrates the effect of Test drug tablet on clinical symptoms in alcoholic liver cirrhosis patients.

TABLE 11

| | | No. of patients showing clinical symptoms (n = 40) | | | | | |
|---|---|---|---|---|---|---|---|
| | | Post treatment | | | | | |
| Symptoms | Pretreatment | 1st month | 2nd month | 3rd month | 4th month | 5th month | 6th month |
| Asthenia (weakness) | 36 | 31 (NS) | 26 ($p < 0.014$) | 18 ($p < 0.0001$) | 16 ($p < 0.0001$) | 12 ($p < 0.0001$) | 11 ($p < 0.0001$) |
| Easy fatigability | 36 | 26 ($p < 0.015$) | 23 ($p < 0.0001$) | 15 ($p < 0.0001$) | 12 ($p < 0.0001$) | 10 ($p < 0.0001$) | 10 ($p < 0.0001$) |
| Tiredness | 32 | 20 ($p < 0.009$) | 18 ($p < 0.0001$) | 10 ($p < 0.0001$) | 8 ($p < 0.0001$) | 7 ($p < 0.0001$) | 6 ($p < 0.0001$) |
| Nausea | 25 | 17 (NS) | 13 ($p < 0.0001$) | 8 ($p < 0.0001$) | 8 ($p < 0.0001$) | 7 ($p < 0.0001$) | 7 ($p < 0.0001$) |
| Anorexia | 27 | 18 ($p < 0.003$) | 9 ($p < 0.0001$) | 9 ($p < 0.0001$) | 7 ($p < 0.0001$) | 6 ($p < 0.0001$) | 6 ($p < 0.0001$) |
| Abdominal discomfort | 24 | 13 ($p < 0.02$) | 8 ($p < 0.001$) | 8 ($p < 0.0001$) | 7 ($p < 0.0001$) | 6 ($p < 0.0001$) | 5 ($p < 0.001$) |
| Abdominal pain/tenderness at right hypochondriac area) | 18 | 7 ($p < 0.015$) | 4 ($p < 0.0009$) | 4 ($p < 0.0002$) | 3 ($p < 0.0002$) | 2 ($p < 0.0001$) | 2 ($p < 0.0001$) |
| Increased stool frequency with colour of the stool | 8 | 5 (NS) | 4 (NS) | 3 (NS) | 2 (NS) | 2 (NS) | 0 ($p < 0.05$) |
| Muscle cramps | 16 | 7 ($p < 0.047$) | 4 ($p < 0.004$) | 4 ($p < 0.001$) | 3 ($p < 0.001$) | 3 ($p < 0.004$) | 2 ($p < 0.001$) |

Table 12 illustrates the effect of Test drug tablet on physical signs in alcoholic liver cirrhosis patients.

TABLE 12

| | | Post treatment | | | | | |
|---|---|---|---|---|---|---|---|
| Physical signs | Pre treatment | $1^{st}$ month | $2^{nd}$ month | $3^{rd}$ month | $4^{th}$ month | $5^{th}$ month | $6^{th}$ month |
| Muscle wasting | 20 | 18 (NS) | 12 (NS) | 12 (NS) | 9 ($p < 0.019$) | 9 ($p < 0.019$) | 7 ($p < 0.004$) |
| Jaundice | 21 | 17 (NS) | 17 (NS) | 11 ($p < 0.039$) | 8 ($p < 0.005$) | 8 ($p < 0.005$) | 7 ($p < 0.001$) |
| Anaemia | 20 | 17 (NS) | 14 (NS) | 11 (NS) | 8 ($p < 0.09$) | 8 ($p < 0.009$) | 6 ($p < 0.009$) |
| Oedema | 15 | 16 (NS) | 11 (NS) | 7 (NS) | 5 ($p < 0.018$) | 5 ($p < 0.018$) | 4 ($p < 0.018$) |
| Ascites | 16 | 12 (NS) | 11 (NS) | 8 (NS) | 6 ($p < 0.023$) | 6 ($p < 0.023$) | 4 ($p < 0.023$) |
| Hepatomegaly (severity score expressed as Mean ± SD) | 1.80 ± 0.88 | 1.18 ± 0.50 (NS) | 1.13 ± 0.46 | 1.08 ± 0.47 | 0.90 ± 0.44 | 0.88 ± 0.40 | 0.85 ± 0.43 ($p < 0.001$) |

Statistical analysis was carried out using Fisher's exact test for all parameters, except hepatomegaly. Analysis for hepatomegaly was carried out using Friedman's test followed by Dunnett's multiple comparison Post-hoc test.

Table 13 illustrates the effect of Test drug tablet on liver function test parameters.

TABLE 13

| Efficacy parameter | Pre-treatment | Post-treatment | Significance |
|---|---|---|---|
| Alanine transaminase (ALT) (IU/L) | 95.88 ± 87.15 | 55.96 ± 38.87 | $p < 0.005$ |
| Aspartate transaminase (AST) (IU/L) | 123.20 ± 64.74 | 74.82 ± 48.52 | $p < 0.005$ |
| Total bilirubin (mg/dl) | 3.11 ± 2.15 | 1.22 ± 1.15 | $p < 0.005$ |
| Alkaline phosphatase (ALP) (IU/L) | 232.30 ± 102.30 | 200.30 ± 82.53 | $p < 0.005$ |
| Albumin (gm/dl) | 3.33 ± 0.69 | 3.62 ± 0.66 | $p < 0.005$ |
| Prothrombin time (INR) | 1.43 ± 0.32 | 1.18 ± 0.18 | $p < 0.005$ |

All the values are expressed as Mean ± SD. Statistical analysis was carried out using Students paired t-test.

Table 14 illustrates the effect of Test drug on withdrawal symptoms.

TABLE 14

| Symptoms | No. of patients | % relief | SD ± SE | t | P |
|---|---|---|---|---|---|
| Tremors | 152 | 80.54% | 0.201 | 8.02 | <0.001 |
| Headache | 194 | 100% | 0 | — | <0.001 |
| Restlessness | 201 | 91.2% | 0.239 | 9.01 | <0.001 |
| Anxiety | 166 | 90.56% | 0.226 | 8.74 | <0.001 |

It was observed that by treating with Test drug for two months, about 60% of the patients could come out of their addiction whereas others had reduced their addictions. When the treatment was continued, 80% of them could completely give up their addiction and recurrence rate was negligible (0.1%).

Discussion:

The present clinical study observed a significant reduction in the clinical symptom scores of asthenia, easy fatigability, tiredness, nausea, anorexia, abdominal discomfort, abdominal pain, stool frequency, and muscle cramps after treatment with Test drug tablet over a period. All these effects strengthen liver, regulate body metabolism and ultimately inhibit further liver cell damage by favoring regeneration. A significant reduction in physical sign scores was observed with muscle wasting, jaundice, anemia, edema, ascites, and hepatomegaly at the end of treatment with Test drug tablet. A significant reduction in liver function test parameters of alanine transaminase, aspartate transaminase, total bilirubin, alkaline phosphatase, an improvement in albumin, and prothrombin time were observed at the end of therapy, as compared to pre-treatment values. There were no clinically significant adverse events during the entire study period. In present study, the efficacy of Test drug on alcoholic liver disease was investigated. In cirrhotic patients treated with Test drug, the serum ALT and AST levels were significantly decreased. This decrease in serum ALT and AST levels in Test drug treated patients in part may be due to the protective effect of Test drug on liver cells following restoration of liver cell membrane permeability. This protective effect indicates reduction in enzymes present in the extra cellular milieu as elevated serum level of ALT and AST may be attributed as damage to the structural integrity of liver. Test drug possesses the ingredients with hepatoprotective effect in cirrhotic patients and this effect may be due to its diuretic, anti-inflammatory, anti-oxidative, immunomodulating as well as restorative effects. In total it is the synergic effect of ingredients of Test drug tablets that help in improving liver function and minimizes symptoms of alcohol addiction.

Conclusion:

Based on the results of the Clinical study, the following conclusions were drawn: Test drug possesses hepatoprotective action and beneficial effects in alcoholic liver diseases; induces natural sleep pattern; reduces withdrawal symptoms; improves will power to give up addiction; and improves appetite.

Example 3: Clinical Study II

Aim of Study:

To study the efficacy of test drug on subjective parameters of alcohol withdrawal.

Patients and Methods 40 diagnosed patients of Madatyaya (Alcohol Withdrawal) who fulfilled the inclusion criteria and consenting, were studied as a single group for a duration of 1 month. Assessment was done before and after the study period.

Inclusion Criteria:

Diagnosed patients of Madatyaya (alcohol withdrawal symptoms), Age between 18-50 years of both genders irrespective of socio-economic status.

Exclusion Criteria:

Subjects suffering from systemic diseases like diabetes mellitus and uncontrolled hypertension, alcoholic liver cirrhosis, ascites; Subjects suffering from organic brain diseases and other psychiatric illnesses; and Subjects suffering from severe withdrawal symptoms like delirium tremens and status epilepticus.

Subjective Parameters:

Samanya madatyaya lakshanas (Clinical features of Madatyaya according to Ayurveda): Complaints of; Aruchi (Reduced Appetite), Prajagara (Insomnia), Bhrama (Giddiness), Pralapa (Delirium), Roopanamasatam Chaiva Darshanam (Hallucinations), Chardi (Vomiting), Atisara (Loose stools), Hrillasa (Nausea) and Shareera Kampa (Tremors).

Grading for Samanya Madatyaya Lakshanas:

0 to 3 except for Hrillasa which is rated on scale 0 to 2.

CIWA-AR SCALE: Nausea/vomiting, anxiety, paroxysmal sweats, tactile disturbances, visual disturbances, visual disturbances, tremors, agitation, orientation and clouding of sensorium, auditory disturbances and headache. Each criterion is rated on a scale from 0 to 7, except for orientation and clouding of sensorium which is rated on scale 0 to 4. Scores are added up to all 10 criteria.

Diagnostic Criteria:

Diagnosis was based on the general features of alcohol withdrawal mentioned in Ayurvedic texts and ICD-10 Criteria for alcohol withdrawal. Diagnostic criteria for Alcohol withdrawal according to ICD-10. The general criteria for withdrawal should be met i.e. there must be a clear evidence of recent cessation or reduction of alcohol after repeated, and usually prolonged or high dose, use of alcohol; and symptoms and signs are not accounted for by a medical disorder unrelated to alcohol, and not better accounted for, by another mental or behavioral disorder.

Any three of the following signs must be present: Tremor of the tongue, eyelids or outstretched hands; Sweating; Nausea, retching and vomiting; Tachycardia or hypertension; Psychomotor agitation; Headache; Insomnia; Malaise or weakness; Transient visual, tactile or auditory hallucinations or illusions and Grand mal convulsions.

Patients were screened using CIWA-AR scale and Samanya Madatyaya Lakshanas. Single group study, patients were selected on the basis of convenience sampling and treated with test drug. 2 tablets (2×500 mg) twice daily swallowed with water after food for one month. The patients were assessed on day 1 before treatment, and on $3^{rd}$ day, $7^{th}$ day, and $30^{th}$ day after treatment.

Statistical Analysis:

Statistical analysis was done using SPSS VER.20. Friedman's test was applied to analyze the significance of the change in subjective parameters. Wilcoxon's signed rank test was applied for post hoc which showed significance in Friedman's test, to interpret the time of significant change.

Observations:

45 patients who presented themselves at the OPD with the complaints of alcohol related problems were screened with CIWA-Ar scale and 42 patients who fulfilled the inclusion criteria were selected and registered for the study. Out of 42 patients, 2 patients withdrew from the study, due to personal constraints.

The maximum number of patients were in the age group of 41-50 years (50%; 20 patient), started consuming alcohol due to peer pressure (60%; 24 patients), had a history of alcohol consumption during the second decade of life (77.5%; 31 patient), had early morning use of alcohol (65%; 26 patients), had history of daily consumption of alcohol (90%; 36 patients), and consumed about 180-360 ml of alcohol (42.5%; 17 patients).

Nausea/vomiting (90%; 36 patients), Tremors (100%; 40 patients), Paroxysmal sweats (37.5%; 15 patients), Anxiety (100%; 40 patients), Agitation (65%; 26 patients), Orientation disturbances (20%; 8 patients), Tactile Disturbances (12.5%; 5 patients), Auditory disturbances (25%; 10 patients), Visual disturbances (12.5%; 5 patients), Headache (67.5%; 27 patients), Aruchi (80%; 32 patients), Atisara (22.5%; 9 patients), Bhrama (62.5%; 25 patients), Prajagara (100%; 40 patients) was noted in this study.

Results:

There was Statistical significant result in subjective symptoms of Madatyaya like, Nausea/vomiting (50%; p<0.001), Tremors (50%; p<0.001), Paroxysmal sweats (47.71%; p<0.001), Anxiety (50%; p<0.001), Agitation (50%; p<0.001), Orientation (44.5%; p 0.014), Tactile Disturbances (42.10%; p 0.046), Auditory disturbances (45.36%; p 0.005), Visual disturbances (42.10%; p 0.046), Headache (48.48%; p<0.001), Aruchi (50%; p<0.001), Atisara (45.36%; p 0.005), Bhrama (48.48%; p<0.001), Prajagara (50%; p<0.001)

Discussion:

Alcohol has an effect on multiple neurotransmitter systems in the brain. When alcohol intake is stopped abruptly; acute alcohol ingestion has an inhibitory effect at N-methyl-D-aspartate (NMDA) receptors, reducing excitatory glutamatergic transmission and has an agonistic effect at gamma-aminobutyric acid type-A (GABAA) receptors. During prolonged exposure to alcohol, NMDA receptors are upregulated and GABA receptors are downregulated, leading to tolerance. The roles are reversed during abstinence, with enhanced NMDA receptor function; reduced GABAergic transmission and dysregulation of the dopaminergic system, leading to many of the symptoms and signs of AWS. The most severe manifestations of withdrawal include delirium tremens, hallucinations, and seizures. In ayurvedic context, alcohol withdrawal may present with following symptoms like, vitiation of Vata causes headache, insomnia, vivid dreams, hallucinations, anxiety, restlessness, constipation & tremor and vitiation Pitta causes gastric disturbances, excessive sweating, giddiness, aggression & violence and vitiation of Kapha cause excessive sleep, depression, lethargy, heaviness in the body, nausea & vomiting while vitiation of Tridosha causes combination of the above clinical feature. In general, Vata-pitta predominant Tridoshaja (bodily humor) and Rajas (psychic principle) is the main Manodosha (psychic humors) involved in the pathology of alcohol dependence & withdrawal.

Conclusion:

Overall it was concluded from the statistical analysis and clinical evaluation, all the withdrawal symptoms subsided by 7 days. Study continued further statistically there were significant changes seen in impaired liver function test; the test drug has combined effect on Nervous system, gastrointestinal system, and Hepato-biliary system. It is also found useful in reducing the alcohol withdrawal symptoms.

Gastrointestinal Symptoms:

Anorexia, Nausea/vomiting, Diarrhea—reduced 3rd day of treatment, Neurological Symptoms: Tremors, Anxiety, Insomnia—Reduced significantly at the end of $4^{th}$ day (30 patients), but 5 patients persisted with fine hand tremors and Insomnia, even after the treatment because of chronic dependence of alcohol i.e., protracted withdrawal, it may require up to 6 months to get recovered.

Cognitive Disturbances:

Auditory, Visual and Tactile Hallucinations significant changes seen by $4^{th}$ day. In this study patients were well motivated about the ill effects of alcohol by motivation along with anti-craving property of test drug is observed and helps in relapse prevention.

Example 4: Clinical Trial (III)

Aim of the Study:

To evaluate the efficacy of the test drug in smoking de-addiction.

Patients and Method

Sixty-four addicts willing to withdraw smoking, presenting with varying symptoms, of the age group 20 and 60 years were randomly selected. All the patients were males. Test drug tablets were administered at a dose of 2 tablets twice daily (1 gram bd) swallowed with water after food for duration of 45 days. Patients were evaluated on 15th, $30^{th}$ and $45^{th}$ day.

Figure 8:
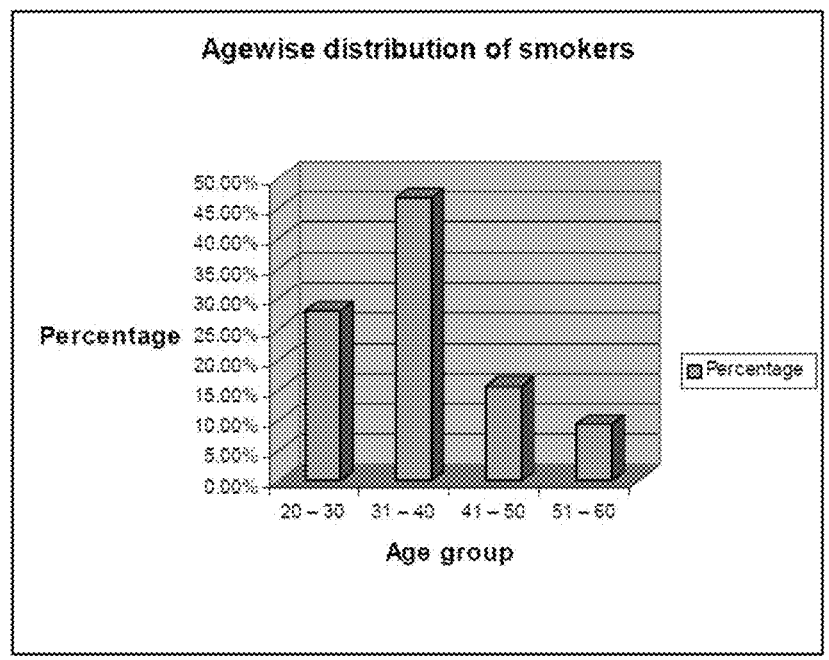
FIG. 8 is a graphical representation depicting the percentage incidence in various age groups.

Observations and Results:

Table 15 and FIG. 8 depict the percentage incidence in various age groups.

TABLE 15

Percentage incidence with age wise distribution

| Age Group (years) | Male | Percentage |
|---|---|---|
| 20-30 | 18 | 28.125% |
| 31-40 | 30 | 46.875% |
| 41-50 | 10 | 15.625% |
| 51-60 | 06 | 9.375% |

Figure 9:
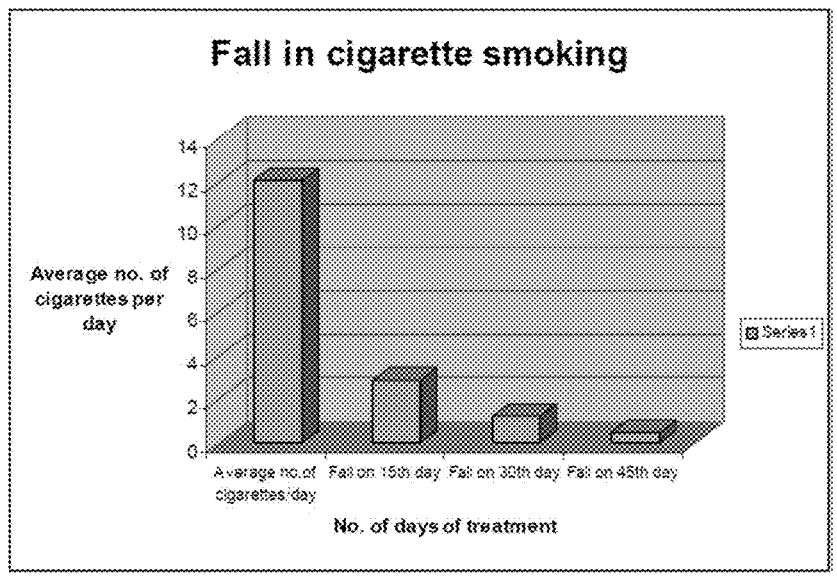
FIG. 9 is a graphical representation depicting the percentage incidence of various symptoms that the smokers had when the treatment was started.

Table 16 depicts the percentage incidence of various symptoms that the smokers had when the treatment was started. FIG. 9 is a graphical representation of the fall in cigarette smoking over a period.

TABLE 16

Percentage incidence with symptom wise distribution

| | Symptoms | No. of cases | Percentage (%) |
|---|---|---|---|
| 1. | Cough | 31 | 48.4 |
| 2. | Exertional dyspnoea | 25 | 39.1 |
| 3. | Discoloration of oral mucosa | 64 | 100.0 |
| 4. | Loss of appetite | 21 | 32.81 |
| 5. | Emotional disturbances | 48 | 75.0 |
| 6. | Disturbed sleep | 45 | 70.3 |
| 7. | Headache | 18 | 28.1 |
| 8. | Constipation | 50 | 78.1 |
| 9. | Acid eructation | 32 | 50.0 |
| 10. | Dry mouth | 51 | 79.7 |

Results:

The results were assessed in the following two stages: reduction in the quantity of cigarettes smoked per day; and improvement in the symptoms presented.

Reduction in the Quantity of Cigarettes Smoked Per Day:

Almost all the patients could reduce the quantity of cigarettes that they were smoking. Maximum response could be observed by the end of 15 days itself. About 72.2% of smokers could stop smoking completely by the end of 45 days. Table 17 depicts the reduction in the quantity of cigarettes smoked per day.

TABLE 17

Reduction in the quantity of cigarettes smoked per day

| No. of individuals | Average no. of cigarettes/day | % Fall on 15th day | % Fall on 30th day | % Fall on 45th day | Success rate |
|---|---|---|---|---|---|
| 64 | 12.1 | 76.0 | 89.93 | 95.81 | 88.70% |

Improvement in the Symptoms Presented:

All the cases included in the present study showed a considerable improvement in their symptoms and signs. Table 18 depicts the scale which was used to assess the response in individual patients.

TABLE 18

| | | |
|---|---|---|
| A. | 40 percent or less response | Fair |
| B. | Over 40 to 70 percent response | Good |
| C. | Over 70 percent response up to complete relief | Excellent |
| D. | Symptoms remained the same | No improvement |

Figure 10:
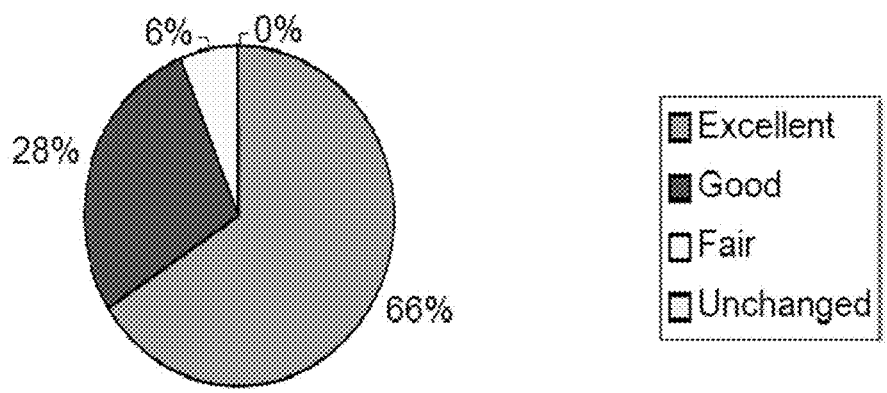
FIG. 10 is a pie chart depicting the percentage response to Test drug.

Table 19 depict the response to medication with Test drug. FIG. 10 is a pie chart depicting the percentage response to Test drug.

TABLE 19

Percentage response to Test drug

| Response | No. of cases | Percentage (%) |
|---|---|---|
| Excellent | 42 | 65.625 |
| Good | 18 | 28.125 |
| Fair | 04 | 6.25 |
| Unchanged | 00 | 00 |

The Test drug administered subjects were observed to be completely free from any side effects.

Discussion:

Based on the results it was observed that the test drug had the following effect on patients with nicotine addiction: alleviation of clinical symptoms caused by the habit of smoking; protection of vital organs from the damage that may be caused by the smoking; developing the will power to quit smoking; and minimizing withdrawal effects. The patients were observed for the relapse of smoking habit. They were managed with additional procedures like Yoga, Pranayama, pyramid therapy and counseling. It is very interesting to note that the relapse rate was less than 1%.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. An oral composition for prevention, treatment and management of substance addiction, comprising a therapeutically effective amount of *Phyllanthus niruri*, *Eclipta alba*, *Boerhavia diffusa*, *Swertia chirata*, *Embelia ribes*, *Acacia catechu*, *Plumbago zeylanica*, *Terminalia arjuna*, *Pueraria tuberosa*, *Picrorhiza kurroa*, *Commiphora mukul*, *Emblica officinalis*, *Terminalia chebula*, *Terminalia bellerica*, *Piper longum*, *Piper nigrum*, *Zingiber officinalis*, *Aegle marmelos*, *Premna mucronata*, *Oroxylum indicum*, *Stereospermum suaveolens*, *Gmelina arborea*, *Solanum indicum*, *Solanum xanthocarpum*, *Tribulus terrestris*, *Uraria picta*, *Desmodium gangeticum*, *Bacopa monnieri*, *Convolvulus pluricaulis*, *Mucuna pruriens*, *Nardostachys jatamansi*, *Rauwolfia serpentina*, *Withania somnifera*, *Acorus calamus*, *Santalum album*, *Pterocarpus santalinus*, *Glycyrrhiza glabra*, *Inula racemose*, *Sida cordifolia*, *Cinnamomum zeylanica*, *Elettaria cardamomum*, *Ocimum sanctum*, *Tinospora cordifolia*, *Vetiveria zizanioides*, *Hemidesmus indicus*, *Pluchea lanceolate*, *Cassia fistula*, *Prunus cerasoides*, *Rubia cordifolia*, *Ricinus communis* and *Mesua ferrea*, or extract thereof; Shilajit; Rasasindura; and at least one bhasma.

2. The composition as claimed in claim 1, wherein said bhasma is selected from the group consisting of Mukta shukti bhasma, Swarna makshika bhasma, Rajata bhasma, Pravala bhasma, Shringa bhasma, Yashada bhasma, Vanga bhasma, Shankha bhasma, Loha bhasma, Abhraka bhasma, Tamra bhasma and Mandura bhasma.

3. The composition as claimed in claim 1, wherein *Phyllanthus niruri* is present in an amount in the range of 4 to 8 wt. %; *Eclipta alba* is present in an amount in the range of 2 to 6 wt. %; *Boerhavia diffusa* is present in an amount in the range of 2 to 6 wt. %; *Swertia chirata* is present in an amount in the range of 2 to 6 wt. %; *Embelia ribes* is present in an amount in the range of 2 to 6 wt. %; *Acacia catechu* is present in an amount in the range of 2 to 6 wt. %; *Plumbago zeylanica* is present in an amount in the range of 6 to 10 wt. %; *Terminalia arjuna* is present in an amount in the range of 6 to 10 wt. %; *Pueraria tuberosa* is present in an amount in the range of 2 to 6 wt. %; *Picrorhiza kurroa* is present in an amount in the range of 6 to 10 wt. %; *Commiphora mukul* (Guggulu) is present in an amount of ≤3 wt. %; Shilajit is present in an amount of ≤3 wt. %; and Rasasindura is present in an amount of ≤1 wt. %, of the total composition.

4. The composition as claimed in claim 2, wherein Mukta shukti bhasma is present in an amount of ≤1 wt. %; Swarna makshika bhasma is present in an amount of ≤1 wt. %; Rajata Bhasma is present in an amount of ≤1 wt. %; Pravala bhasma is present in an amount of ≤1 wt. %; Shringa bhasma is present in an amount of ≤1 wt. %; Yashada bhasma is present in an amount of ≤1 wt. %; Vanga bhasma is present in an amount of ≤1 wt. %; Shankha bhasma is present in an amount of ≤1 wt. %; Loha bhasma is present in an amount of ≤2 wt. %; Abhraka bhasma is present in an amount of ≤2 wt. %; Tamra bhasma is present in an amount of ≤1 wt. %; and Mandura bhasma is present in an amount of ≤1 wt. %, of the total composition.

5. The composition as claimed in claim 1, wherein *Emblica officinalis* is present in an amount of ≤1 wt. %; *Terminalia chebula* is present in an amount of ≤1 wt. %; *Terminalia bellerica* is present in an amount of ≤1 wt. %; *Piper longum* is present in an amount of ≤1 wt. %; *Piper nigrum* is present in an amount of ≤1 wt. %; *Zingiber officinalis* is present in an amount of ≤1 wt. %; *Aegle marmelos* is present in an amount of ≤1 wt. %; *Premna mucronata* is present in an amount of ≤1 wt. %; *Oroxylum indicum* is present in an amount of ≤1 wt. %; *Stereospermum suaveolens* is present in an amount of ≤1 wt. %; *Gmelina arborea* is present in an amount of ≤1 wt. %; *Solanum indicum* is present in an amount of ≤1 wt. %; *Solanum*

*xanthocarpum* is present in an amount of ≤1 wt. %; *Tribulus terrestris* is present in an amount of ≤1 wt. %; *Uraria picta* is present in an amount of ≤1 wt. %; *Desmodium gangeticum* is present in an amount of <1 wt. %; *Bacopa monnieri* is present in an amount of <1 wt. %; *Convolvulus pluricaulis* is present in an amount of <1 wt. %; *Mucuna pruriens* is present in an amount of <1 wt. %; *Nardostachys jatamansi* is present in an amount of <1 wt. %; *Rauwolfia serpentina* is present in an amount of ≤1 wt. %; *Withania somnifera* is present in an amount of ≤1 wt. %; *Acorus calamus* is present in an amount of ≤1 wt. %; *Santalum album* is present in an amount of ≤1 wt. %; *Pterocarpus santalinus* is present in an amount of ≤1 wt. %; *Glycyrrhiza glabra* is present in an amount of ≤1 wt. %; *Inula racemosa* is present in an amount of ≤1 wt. %; *Sida cordifolia* is present in an amount of ≤1 wt. %; *Cinnamomum zeylanica* is present in an amount of ≤1 wt. %; *Elettaria cardamomum* is present in an amount of ≤1 wt. %; *Ocimum* sanctum is present in an amount of ≤1 wt. %; *Tinospora cordifolia* is present in an amount of ≤1 wt. %; *Vetiveria zizanioides* is present in an amount of ≤1 wt. %; *Hemidesmus indicus* is present in an amount of ≤1 wt. %; *Pluchea lanceolata* is present in an amount of ≤1 wt. %; *Cassia fistula* is present in an amount of ≤1 wt. %; *Prunus cerasoides* is present in an amount of ≤1 wt. %; *Rubia cordifolia* is present in an amount of ≤1 wt. %; *Ricinus communis* is present in an amount of ≤1 wt. %; and *Mesua ferrea* is present in an amount of ≤1 wt. %, of the total composition.

6. The composition as claimed in claim 1, further comprising Gum acacia.

7. The composition as claimed in claim 6, wherein Gum acacia is present in an amount in the range of 8 to 12 wt. % of the total composition.

8. The composition as claimed in claim 1, said composition comprising *Phyllanthus niruri; Eclipta alba; Boerhavia diffusa; Swertia chirata; Embelia ribes; Acacia catechu; Plumbago zeylanica; Terminalia arjuna; Pueraria tuberosa; Picrorhiza kurroa; Commiphora mukul; Emblica officinalis; Terminalia chebula; Terminalia bellerica; Piper longum; Piper nigrum; Zingiber officinalis; Aegle marmelos; Premna mucronata; Oroxylum indicum; Stereospermum suaveolens; Gmelina arborea; Solanum indicum; Solanum xanthocarpum; Tribulus terrestris; Uraria picta; Desmodium gangeticum; Bacopa monnieri; Convolvulus pluricaulis; Mucuna pruriens; Nardostachys jatamansi; Rauwolfia serpentina; Withania somnifera; Acorus calamus; Santalum album; Pterocarpus santalinus; Glycyrrhiza glabra; Inula racemosa; Sida cordifolia; Cinnamomum zeylanica; Elettaria cardamomum; Ocimum sanctum; Tinospora cordifolia; Vetiveria zizanioides; Hemidesmus indicus; Pluchea lanceolata; Cassia fistula; Prunus cerasoides; Rubia cordifolia; Ricinus communis; Mesua ferrea*; Shilajit; Rasasindura; Mukta shukti bhasma; Swarna makshika bhasma; Rajata Bhasma; Pravala bhasma; Shringa bhasma; Yashada bhasma; Vanga bhasma; Shankha bhasma; Loha bhasma; Abhraka bhasma; Tamra bhasma; Mandura bhasma; and Gum acacia.

9. The composition as claimed in claim 1, wherein said composition is in the form of at least one oral dosage form selected from the group consisting of tablets, pellets, lozenges, granules, suspensions and capsules.

10. The composition as claimed in claim 9, wherein said composition is in the form of tablet.

11. The composition as claimed in claim 10, wherein said composition is in the form of 500 mg tablet.

12. The composition as claimed in claim 1, wherein said composition is used in the treatment of alcohol addiction and associated complication.

13. The composition as claimed in claim 1, wherein said composition is used in the treatment of tobacco addiction and associated complication.

14. The composition as claimed in claim 1, wherein said composition is used in alleviating withdrawal symptoms.

15. A process for preparation of the composition claimed in claim 1 or 2, said process comprising
levigating a mixture of at least one bhasma; Rasasindura; *Commiphora mukul*; and Shilajit in a grinder to obtain a levigated mixture;
adding herbs to said levigated mixture and grinding, wherein said herbs comprise whole plant of *Phyllanthus niruri*, whole plant of *Eclipta alba*, roots of *Boerhavia diffusa*, whole plant of *Swertia chirata*, fruit of *Embelia ribes*, heartwood of *Acacia catechu*, root of *Plumbago zeylanica*, stem bark of *Terminalia arjuna*, tuber of *Pueraria tuberosa*, root of *Picrorhiza kurroa*, fruit of *Emblica officinalis*, fruit of *Terminalia chebula*, fruit of *Terminalia bellerica*, fruit of *Piper longum*, fruit of fruit of *Tribulus terrestris*, fruit of *Piper nigrum*, rhizome of *Zingiber officinalis*, rhizome of *Acorus calamus*, rhizome of *Nardostachys jatamansi*, root of *Aegle marmelos*, root of *Premna mucronata*, root of *Glycyrrhiza glabra*, root of *Inula racemosa*, root of *Sida cordifolia*, root of *Rauwolfia serpentina*, root of *Rubia cordifolia*, root of *Vetiveria zizanioides*, root of *Hemidesmus indicus*, root of *Pluchea lanceolata*, root of *Elettaria cardamomum*, root of *Withania somnifera*, root of *Oroxylum indicum*, root of *Stereospermum suaveolens*, root of *Uraria picta*, root of *Desmodium gangeticum*, root of *Gmelina arborea*, root of *Solanum indicum*, root of *Solanum xanthocarpum*, whole plant of *Bacopa monnieri*, whole plant of *Convolvulus pluricaulis*, seeds of *Mucuna pruriens*, heartwood of *Santalum album*, heartwood of *Prunus cerasoides*, heartwood of *Pterocarpus santalinus*, stem bark of *Cinnamomum zeylanica*, stem bark of *Cassia fistula*, leaves of *Ocimum sanctum*, leaves of *Ricinus communis*, stem of *Tinospora cordifolia* and stamen of *Mesua ferrea*;
adding grinding decoction to said grinder while continuing grinding to obtain a ground mass, wherein said grinding decoction comprises a decoction of at least one herb selected from the group consisting of *Phyllanthus niruri* and *Eclipta alba*.

16. The process as claimed in claim 15, wherein said grinding decoction further comprises a decoction of *Asparagus racemosus; Aegle marmelos; Premna mucronata; Oroxylum indicum; Stereospermum suaveolens; Gmelina arborea; Solanum indicum; Solanum xanthocarpum; Tribulus terrestris; Uraria picta; Desmodium gangeticum; Aloe vera; Azadirachta indica; Tinospora cordifolia; Bacopa monnieri; Acorus calamus; Celastrus paniculatus; Nardostachys jatamansi* and *Rauwolfia serpentina*.

17. The process as claimed in claim 15, wherein said bhasma comprises Mukta shukti bhasma; Swarna makshika bhasma; Rajata Bhasma; Pravala bhasma; Shringa bhasma; Yashada bhasma; Vanga bhasma; Shankha bhasma; Loha bhasma; Abhraka bhasma; Tamra bhasma and Mandura bhasma.

18. The process as claimed in claim 15, wherein said levigation is performed for a period of 1 to 4 hours.

19. The process as claimed in claim 15, wherein said grinding is performed at 100 to 150 rpm for a period of 12 to 72 hours.

20. The process as claimed in claim 15, wherein said grinding decoction further comprises Gum acacia.

21. The process as claimed in claim 20, wherein grinding is continued for a period of 1 to 4 hours.

22. The process as claimed in claim 15 or 21, said process further comprising drying and processing of the obtained mass into oral dosage forms.

23. A method for alleviating withdrawal symptoms, said method comprising administering, to a patient in need thereof, a therapeutically effective amount of the composition claimed in claim 1.

24. A method for the treatment of addiction of substances, said method comprising administering, to a patient in need thereof, a therapeutically effective amount of the composition claimed in claim 1.

25. The method as claimed in claim 24, wherein said therapeutically effective amount is 500 to 1000 mg administered at least once a day.

* * * * *